(12) United States Patent
Taniguchi et al.

(10) Patent No.: US 12,384,920 B2
(45) Date of Patent: Aug. 12, 2025

(54) AZO IRON COMPLEX DYE, INK COMPOSITION CONTAINING SAME, AND METHOD FOR PRODUCING AZO IRON COMPLEX DYE

(71) Applicant: ORIENT CHEMICAL INDUSTRIES CO., LTD., Osaka (JP)

(72) Inventors: Masakazu Taniguchi, Neyagawa (JP); Keigo Kanbara, Neyagawa (JP); Hayato Inaba, Neyagawa (JP); Kaori Sato, Neyagawa (JP)

(73) Assignee: ORIENT CHEMICAL INDUSTRIES CO., LTD., Osaka (JP)

( * ) Notice: Subject to any disclaimer, the term of this patent is extended or adjusted under 35 U.S.C. 154(b) by 0 days.

(21) Appl. No.: 18/272,520

(22) PCT Filed: Jan. 27, 2022

(86) PCT No.: PCT/JP2022/002988
§ 371 (c)(1),
(2) Date: Jul. 14, 2023

(87) PCT Pub. No.: WO2022/163736
PCT Pub. Date: Aug. 4, 2022

(65) Prior Publication Data
US 2024/0409746 A1    Dec. 12, 2024

(30) Foreign Application Priority Data
Jan. 29, 2021    (JP) .................... 2021-013104

(51) Int. Cl.
*C09D 11/328* (2014.01)
*B41M 5/00* (2006.01)
(Continued)

(52) U.S. Cl.
CPC .............. *C09B 45/12* (2013.01); *B41M 5/00* (2013.01); *C07C 245/08* (2013.01); *C09B 45/32* (2013.01);
(Continued)

(58) Field of Classification Search
CPC ..... C09B 45/12; C09B 45/32; C09B 67/0047; C09B 67/0033; B41M 5/00; C07C 245/08;
(Continued)

(56) References Cited

U.S. PATENT DOCUMENTS 4,762,524 A * 8/1988 Chambers ........... C09B 62/4403
                                                    8/549
5,319,075 A    6/1994 Berenguer Barra et al.
(Continued)

FOREIGN PATENT DOCUMENTS

JP    S47-044530 B1    8/1970
JP    S51-023518 A     2/1976
(Continued)

OTHER PUBLICATIONS

Apr. 26, 2022 International Search Report issued in International Patent Application No. PCT/JP2022/002988.
(Continued)

*Primary Examiner* — Yaovi M Ameh
(74) *Attorney, Agent, or Firm* — Oliff PLC

(57) ABSTRACT

An azo iron complex dye which does not contain harmful heavy metals, exhibits sufficient solubility in organic solvents for practical use, and exhibits an excellent black color. The azo iron complex dye contains a disazo-monoazo iron complex represented by the following chemical formula (1)

[Chemical Formula 1]

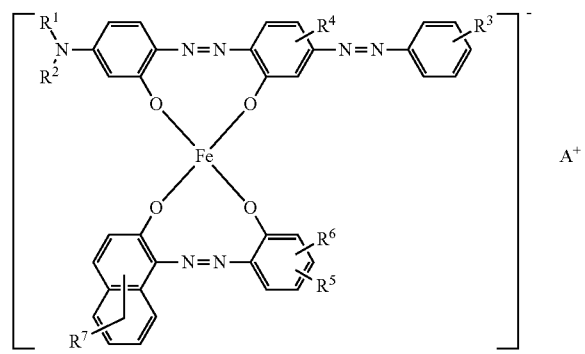

(in the chemical formula (1), $R^1$ and $R^2$ are each independently a straight or branched alkyl group having 3-10 carbon atoms, $R^3$ is an electron-withdrawing group, $R^4$ is a straight
(Continued)

or branched alkyl group having 1-5 carbon atoms or a straight or branched alkoxy group having 1-5 carbon atoms, $R^5$ is a nitro group, a sulfonamide group or a halogen atom, $R^6$ is a hydrogen atom, a straight or branched alkyl group having 1-8 carbon atoms, a nitro group or a halogen atom, $R^7$ is a hydrogen atom or a straight or branched alkyl group having 3-12 carbon atoms, and $A^+$ is a monovalent cation).

10 Claims, 8 Drawing Sheets

(51) Int. Cl.
　　　*C07C 245/08*　　(2006.01)
　　　*C09B 45/12*　　(2006.01)
　　　*C09B 45/32*　　(2006.01)
　　　*C09B 67/22*　　(2006.01)
　　　*C09D 11/037*　　(2014.01)
　　　*C07F 15/02*　　(2006.01)

(52) U.S. Cl.
　　　CPC ........ *C09B 67/0047* (2013.01); *C09D 11/037* (2013.01); *C09D 11/328* (2013.01); *C07F 15/02* (2013.01); *C07F 15/025* (2013.01); *C09B 67/0033* (2013.01)

(58) Field of Classification Search
　　　CPC ..... C09D 11/037; C09D 11/328; C07F 15/02; C07F 15/025
　　　See application file for complete search history.

(56) References Cited

U.S. PATENT DOCUMENTS

| | | |
|---|---|---|
| 5,668,259 A | 9/1997 | Barra et al. |
| 2003/0187234 A1* | 10/2003 | Yasumatsu .............. C09B 29/02 534/715 |

FOREIGN PATENT DOCUMENTS

| | | | |
|---|---|---|---|
| JP | S62-129358 A | 6/1987 | |
| JP | S63-004992 A | 1/1988 | |
| JP | H02-013904 A | 1/1990 | |
| JP | H04-283270 A | 10/1992 | |
| JP | H05-247360 A | 9/1993 | |
| JP | 11217530 A * | 8/1999 | ............ C09D 11/02 |
| JP | H11-217530 A | 8/1999 | |
| JP | 2002080739 A * | 3/2002 | ............ C09B 29/02 |
| JP | 2017222751 A * | 12/2017 | ............ C09B 45/22 |

OTHER PUBLICATIONS

Nov. 12, 2024 Extended European Search Report issued in European Application No. 22745955.9.

Feb. 7, 2025 Office Action issued in Chinese Application No. 202280009818.2.

* cited by examiner

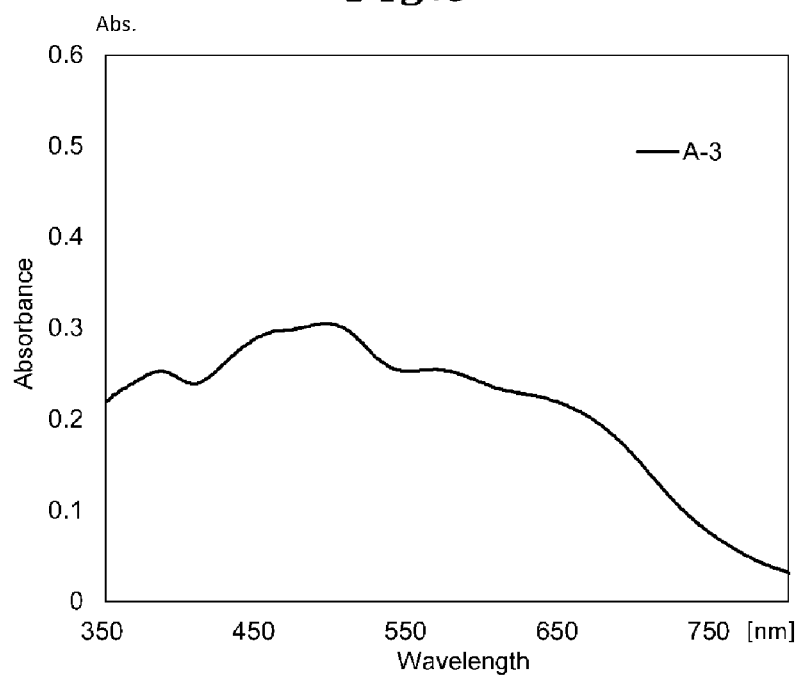

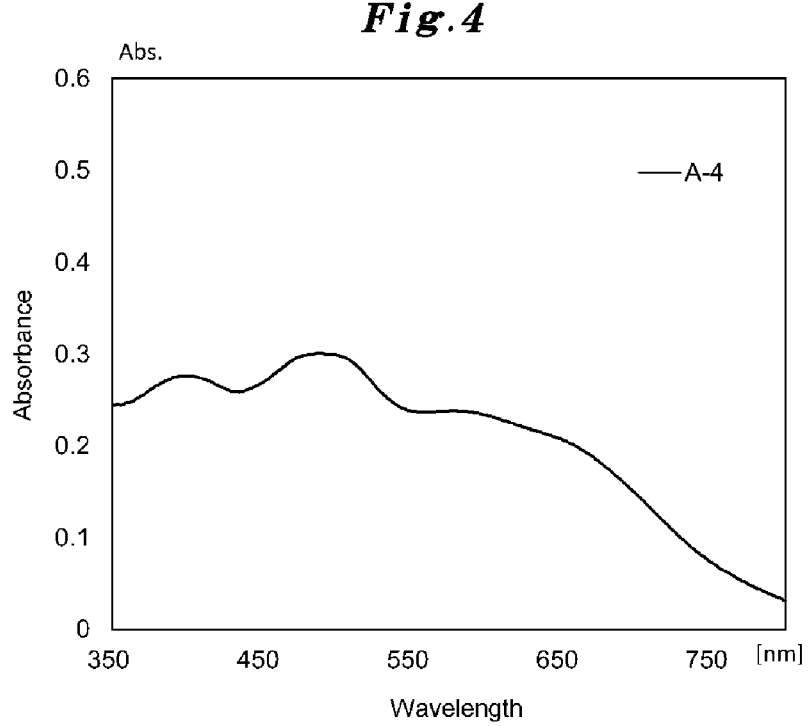

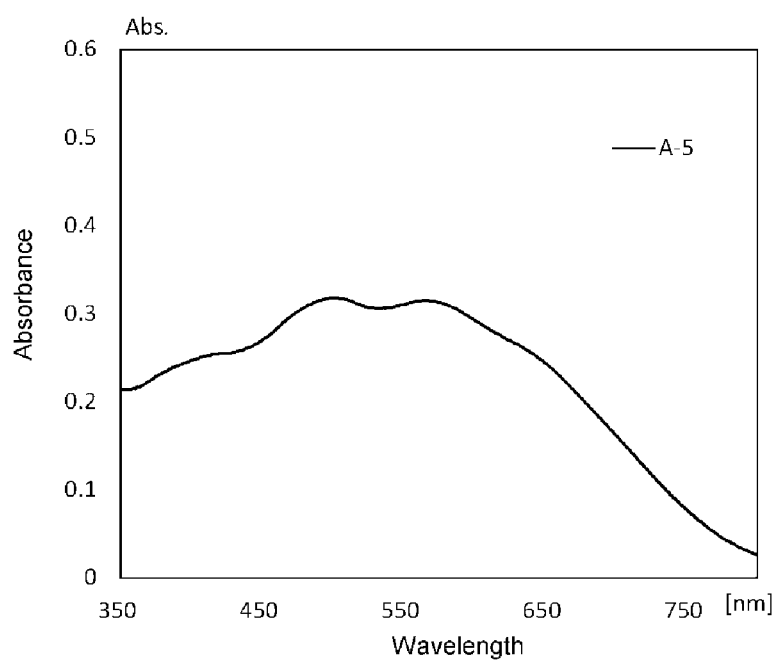

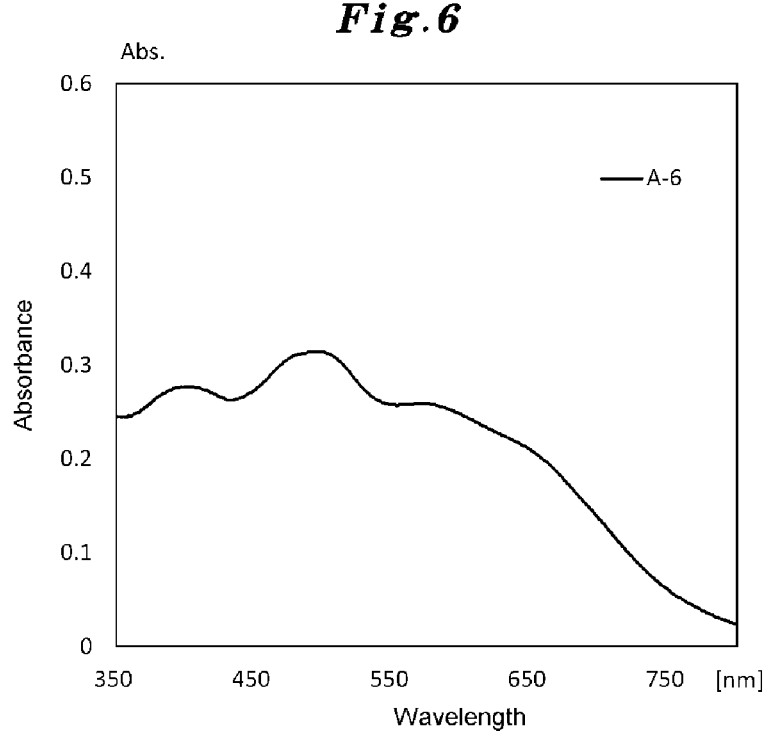

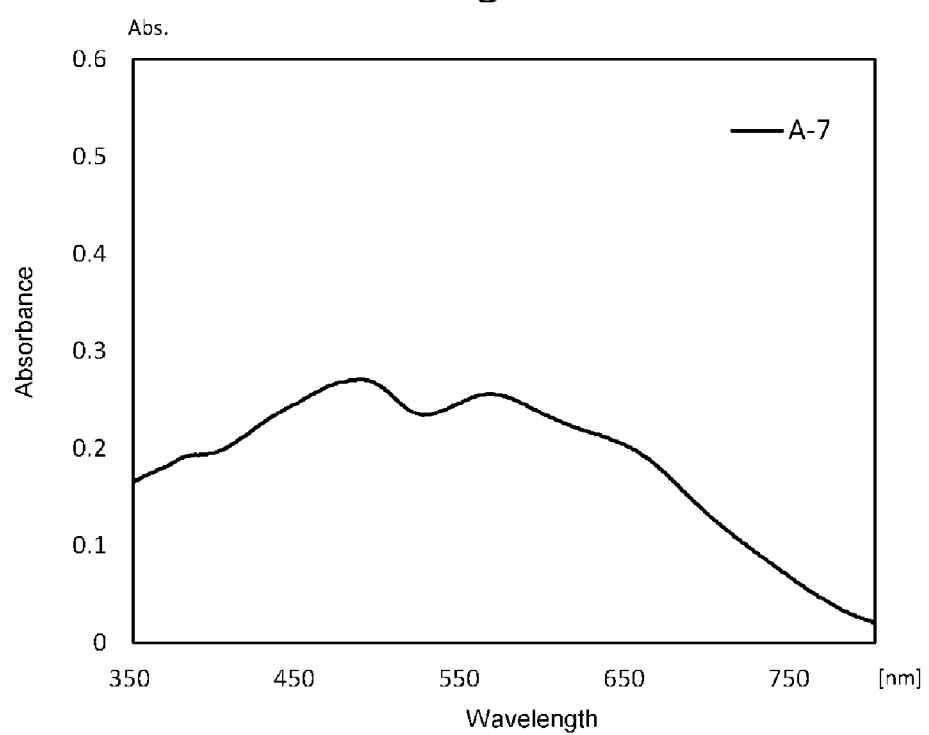

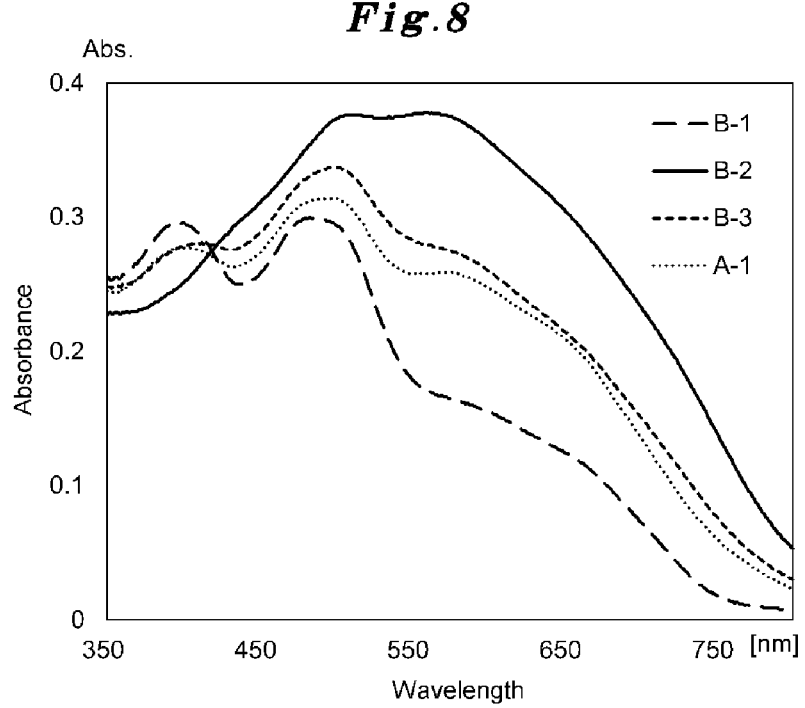

AZO IRON COMPLEX DYE, INK COMPOSITION CONTAINING SAME, AND METHOD FOR PRODUCING AZO IRON COMPLEX DYE

TECHNICAL FIELD

The present invention relates to an azo iron complex dye and an ink composition containing the same, and a method for producing an azo iron complex dye.

BACKGROUND OF THE ART

An ink composition is used by an ink-jet printer, a writing instrument, and a recorder to print on a recording medium or to draw a handwriting. In particular, an ink composition for a continuous-type ink-jet (CIJ) printer widely used in industrial fields is formulated to show high electrical conductivity due to the fact that the CIJ printer is configured to discharge the ink composition onto a recording medium while charging and deflecting it, and also for good adhesion even on a smooth non-absorbent surface like a glass plate, a metal plate, and a plastic plate. Such an ink composition contains a colorant, an organic solvent, and a resin as a fixing agent soluble in an organic solvent.

A colorant contained in the ink composition may include a pigment and a dye. Among colorants, in particular, the demand for a black colorant is the highest. Although a black pigment is less susceptible discoloration due to light and heat, this is poor in color developability and aggregates in the ink composition, resulting in poor storage stability. A black dye has high solubility in an organic solvent and is excellent in color developability and storage stability. However, the black dye deteriorates and discolors due to light and heat, so it has poor in heat and light resistance. As a result, a metal complex dye that exhibits black color and has high heat and light resistance like a black pigment while ensuring high solubility in an organic solvent inherent in the black dye is used as a black colorant.

As an organic solvent contained in the ink composition, in addition to conventionally used a ketone-based organic solvent such as acetone and methyl ethyl ketone, an alcoholic organic solvent such as ethanol and propylene glycol, and an ethereal organic solvent such as propylene glycol monoalkyl ether are also used from the viewpoint of environmental conservation and ensuring safety to the human body.

As a black dye with excellent solubility in an alcoholic organic solvent, for example, an amine salt of an azo chromium complex dye is known. Specifically, for example, the azo chromium complex dye may include C.I. SOLVENT BLACK 23, 27, 28, 29, 35, 45. In addition, the azo chromium complex dye exhibiting black color and soluble in acetone is disclosed in Patent Document 1.

However, the azo chromium complex dye contains chromium as a toxic heavy metal, so that its use is being avoided from the viewpoint of environmental conservation and ensuring safety to the human body. Thus, a metal complex dye that does not contain harmful heavy metals like chromium while having good properties of a metal complex dye is being investigated.

As one of such investigations, a complex mixed dye of three kinds of a disazo compound with iron as a specific complexation agent is proposed in Patent Document 2. Further, in Patent Document 3 a polyazo iron complex dye is described. However, these iron complex dyes are not black, but brown or reddish brown. On the other hand, in Patent Document 4 a monoazo iron complex dye is described. This monoazo iron complex dye has a black purple color, but it is not as black as the azo chromium complex dye.

PRIOR ART DOCUMENT

Patent Document

[Patent Document 1] JPS51-23518A
[Patent Document 2] JPH05-247360A
[Patent Document 3] JPS47-44530B1
[Patent Document 4] JPS63-4992A

SUMMARY OF THE INVENTION

Problems to be Solved by the Invention

The present invention is made to solve the problems, and its object is to provide an azo iron complex dye that does not contain harmful heavy metals and exhibits a good black color with sufficient practical solubility in organic solvents, an ink composition containing the same, and a method for producing an azo iron complex dye.

Means to Solve the Problems

The azo iron complex dye made to solve the above problems contains a disazo-monoazo iron complex represented by the following chemical formula (1):

[Chemical Formula 1]

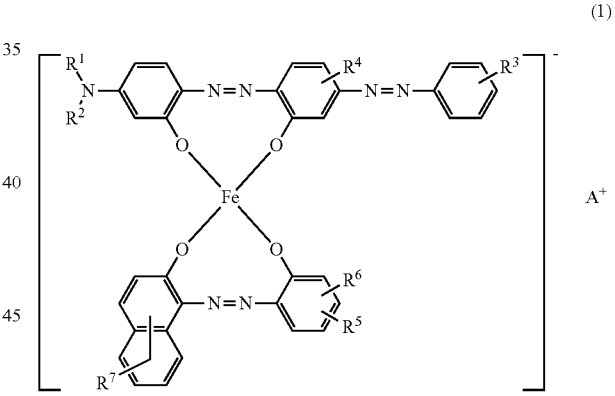

(1)

wherein, in the chemical formula (1), $R^1$ and $R^2$ are each independently a straight or branched alkyl group having 3-10 carbon atoms, $R^3$ is an electron-withdrawing group, $R^4$ is a straight or branched alkyl group having 1-5 carbon atoms or a straight or branched alkoxy group having 1-5 carbon atoms, $R^5$ is a nitro group, a sulfonamide group or a halogen atom, $R^6$ is a hydrogen atom, a straight or branched alkyl group having 1-8 carbon atoms, a nitro group or a halogen atom, $R^7$ is a hydrogen atom or a straight or branched alkyl group having 3-12 carbon atoms, and $A^+$ is a monovalent cation.

In the azo iron complex dye, $R^3$ is bonded at the para-position with respect to the azo group on the same aromatic ring, and may include an electron-withdrawing group selected from the group consisting of a cyano group, a nitro group, an acetyl group, a sulfonamide group, and a halogen atom.

The azo iron complex dye, for example, may contain a monoazo-monoazo iron complex represented by the following chemical formula (2):

[Chemical Formula 2]

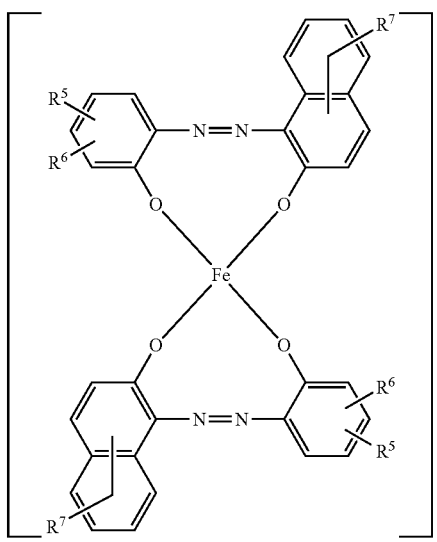

(2)

wherein, in the chemical formula (2), $R^5$-$R^7$ and $A^+$ are the same as ones of the chemical formula (1).

The azo iron complex dye may contain a disazo-disazo iron complex represented by the following chemical formula (3):

[Chemical Formula 3]

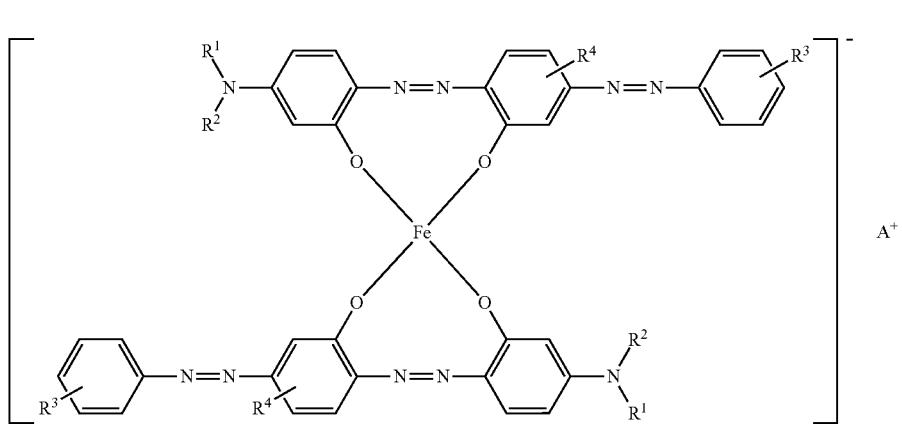

(3)

wherein, in the chemical formula (3), $R^1$-$R^4$ and $A^+$ are the same as ones of the chemical formula (1).

In the azo iron complex dye, for example, the monovalent cation is at least any one of an alkali metal ion, an ammonium ion, and a monovalent ammonium ion having an alkyl group represented by the following chemical formula (4):

[Chemical Formula 4]

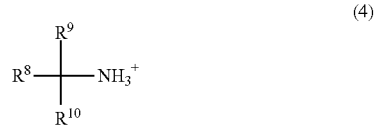

(4)

wherein, in the chemical formula (4), $R^8$ is a straight or branched alkyl group having 1-18 carbon atoms, and $R^9$ and $R^{10}$ are each independently a hydrogen atom or a straight or branched alkyl group having 1-8 carbon atoms.

In the azo iron complex dye, a peak area ratio of the chromatogram obtained by measuring the disazo-monoazo iron complex, the monoazo-monoazo iron complex, and the disazo-disazo iron complex at a wavelength of 254 nm through high performance liquid chromatography may be 20-70:5-80:0-50, respectively.

An ink composition of the present invention contains any one of the azo iron complex dyes shown above and an organic solvent.

The ink composition may be used for an ink-jet printer.

A method for manufacturing the azo iron complex dye comprises: a step for an iron-complexation for preparing an azo iron complex anion by heating a disazo dye represented by the following chemical formula (5):

[Chemical Formula 5]

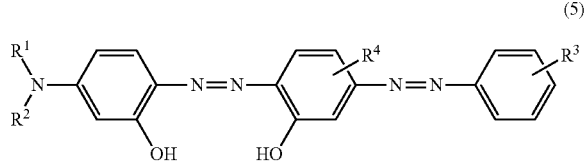

(5)

wherein, in the chemical formula (5), $R^1$ and $R^2$ are each independently a straight or branched alkyl group having 3-10 carbon atoms, $R^3$ is an electron-withdrawing group, $R^4$ is a straight or branched alkyl group having 1-5 carbon atoms or a straight or branched alkoxy group having 1-5 carbon atoms, a monoazo dye represented by the following chemical formula (6):

[Chemical Formula 6]

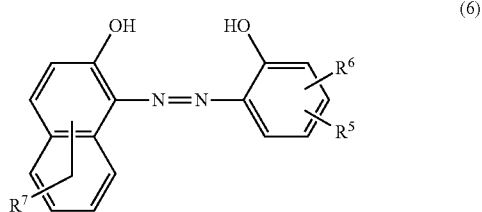

(6)

wherein, in the chemical formula (6). $R^5$ is a nitro group, a sulfonamide group or a halogen atom, $R^6$ is a hydrogen atom, a straight or branched alkyl group having 1-8 carbon atoms, a nitro group or a halogen atom, $R^7$ is a hydrogen atom or a straight or branched alkyl group having 3-12 carbon atoms, and an ironizing agent, in a solvent, and a step for ion-exchanging by reacting an azo iron complex anion, and an alkali metal solution and/or an ammoniation agent to introduce a cation which is combined with the azo iron complex anion, for obtaining a disazo-monoazo iron complex represented by the following chemical formula (1):

[Chemical Formula 1]

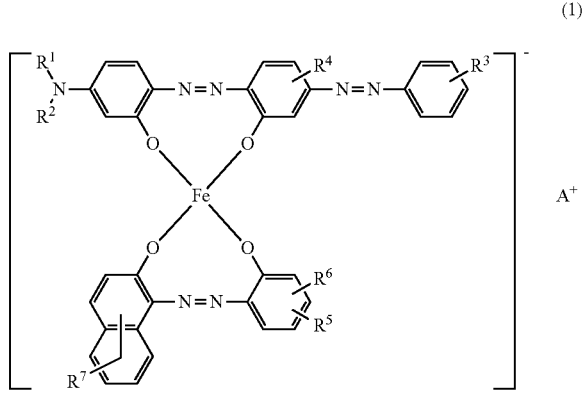

(1)

wherein, in the chemical formula (1), $R^1$-$R^4$ are the same as ones of the chemical formula (5), $R^5$-$R^7$ are the same as ones of the chemical formula (6), and $A^+$ is a monovalent cation.

In the above step for iron-complexation, for example, In the method for producing the azo iron complex dye, for example, the above step for iron-complexation may contain a molar ratio of the disazo dye and the monoazo dye being 2:8 to 8:2.

Effects of the Invention

Since an azo iron complex dye of the present invention does not contain harmful heavy metals such as chromium and cobalt, it can contribute to environmental conservation and also has high safety to the human body compared with an azo chromium complex dye. In addition, the azo iron complex dye exhibits a higher degree of blackness than conventional azo iron complex dyes because of the presence of an azo iron complex having a specific structure. Furthermore, the azo iron complex dye of the present invention has practical dissolution stability in various organic solvents including ketone-based organic solvents, alcoholic organic solvents, and ethereal organic solvents.

Since the ink composition of the present invention contains the azo iron complex dye, the safety for environment and the human body is high, and whether the recording medium is absorbent or non-absorbent, it adheres firmly and does not peel off easily. Thus, it is possible to apply widely as a black colorant for various media including an ink-jet printer, a writing instrument, and a recorder.

According to the method of the present invention for producing the azo iron complex dye, it is possible to produce the azo iron complex dye with high solubility in various organic solvents and high blackness by selecting appropriately substituents that bind to the benzene ring of the ligand of the azo iron complex and cations that bind to the azo iron complex anion and further by adjusting the molar ratio of the disazo dye as a disazo ligand and the monoazo dye as a monoazo ligand.

BRIEF DESCRIPTION OF DRAWINGS

FIG. 3 shows a visible absorption spectrum of the azo iron complex dye A-3 in Example 3 applying the present invention.

FIG. 4 shows a visible absorption spectrum of the azo iron complex dye A-4 in Example 4 applying the present invention.

FIG. 5 shows a visible absorption spectrum of the azo iron complex dye A-5 in Example 5 applying the present invention.

FIG. 6 shows a visible absorption spectrum of the azo iron complex dye A-6 in Example 6 applying the present invention.

FIG. 7 shows a visible absorption spectrum of the azo iron complex dye A-7 in Example 7 applying the present invention.

FIG. 8 shows a visible absorption spectra of the azo iron complex dye A-1 in Example 1 applying the present invention and the azo iron complex dyes B-1-B-3 in Comparative examples 1-3 non-applying the present invention.

MODE FOR CARRYING OUT THE INVENTION

Figure 1:
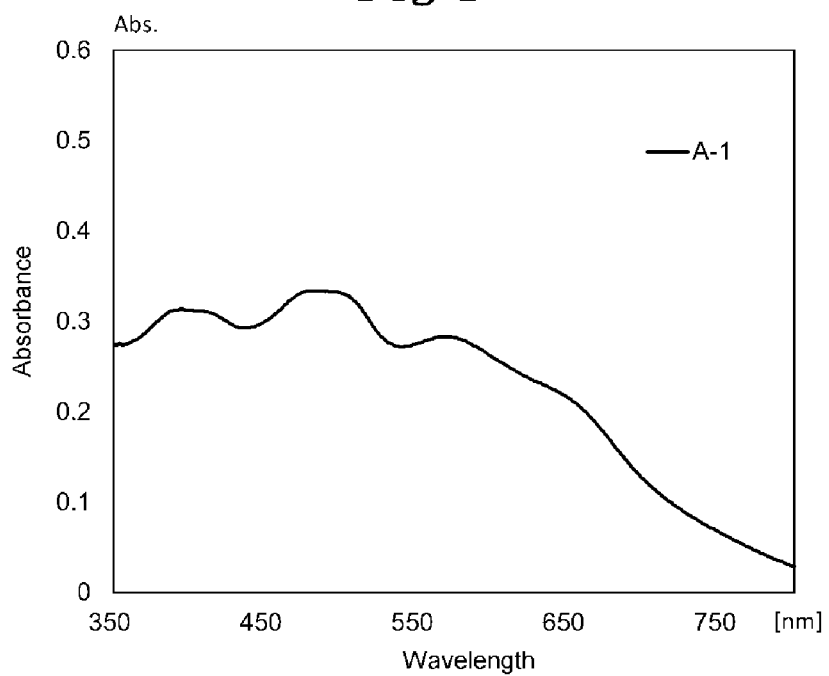
FIG. 1 shows a visible absorption spectrum of the azo iron complex dye A-1 in Example 1 applying the present invention.

Hereunder, the following details the present invention, but the scope of the present invention is not limited to these embodiments. In the specification of the present application. "-" is used in principle to include the numerical values before and after it as lower and upper limits.

(Azo Iron Complex Dye)

An azo iron complex dye of the present invention contains a disazo-monoazo iron complex represented by the following chemical formula (1):

[Chemical Formula 1]

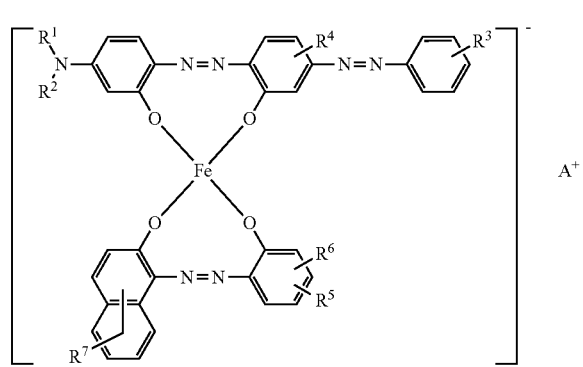

(1)

wherein, in the chemical formula (1). $R^1$ and $R^2$ are each independently a straight or branched alkyl group having 3-10 carbon atoms, $R^3$ is an electron-withdrawing group, $R^4$ is a straight or branched alkyl group having 1-5 carbon atoms or a straight or branched alkoxy group having 1-5 carbon atoms, $R^5$ is a nitro group, a sulfonamide group or a halogen atom, $R^6$ is a hydrogen atom, a straight or branched alkyl group having 1-8 carbon atoms, a nitro group or a halogen atom, $R^7$ is a hydrogen atom or a straight or branched alkyl group having 3-12 carbon atoms, and $A^+$ is a monovalent cation.

As can be seen from the chemical formula (1), the disazo-monoazo iron complex contained in the azo iron complex dye of the present invention has a structure in which an azo iron complex anion containing a trivalent iron and an azo ligand combined with a disazo dye and a monoazo dye in a molar ratio of 1:2 and a monovalent cation are combined.

In the chemical formula (1), $R^1$ and $R^2$ are a straight or branched alkyl group having 3-10 carbon atoms. Specifically, these may include n-propyl group, an isopropyl group, an n-butyl group, an isobutyl group, a sec-butyl group, a tert-butyl group, an n-pentyl group, an isopentyl group, a neopentyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, a 2-methylheptyl group, a 3-methylheptyl group, a 4-methylheptyl group, a 2,2-dimethylhexyl group, a 2,3-dimethylhexyl group, a 2,4-dimethylhexyl group, a 2,5-dimethylhexyl group, a 3,3-dimethylhexyl group, a 3,4-dimethylhexyl group, a 2-ethylhexyl group, a 3-ethylhexyl group, a 2,2,3-trimethylpentyl group, a 2,2,4-trimethylpentyl group, a 2,3,3-trimethylpentyl group, a 2,3,4-trimethylpentyl group, a 2-methyl-3-ethylpentyl group, a 3-methyl-3-ethylpentyl group, a 2,2,3,3-tetramethylbutyl group, an n-nonyl group, an n-decyl group, and a lauryl group. Among these, the n-butyl group, the isobutyl group, the sec-butyl group, the tert-butyl group, the isopentyl group, and the 2-ethylhexyl group are preferable.

In the chemical formula (1), $R^3$ is an electron-withdrawing group, and may include specifically a cyano group, a nitro group, an acetyl group, a sulfonamide group, and a halogen atom. The halogen atom may include fluorine, chlorine, bromine, and iodine. The presence of such an electron-withdrawing group in $R^3$ enhances the bathochromic effect of the azo iron complex dye and hence it can achieve a sufficiently deep black for practical use. When $R^3$ is bonded at the para-position with respect to the azo group on the same aromatic ring, it is preferable in terms of deepening the color.

The disazo-monoazo iron complex is specifically represented by the following chemical formula (7):

[Chemical Formula 7]

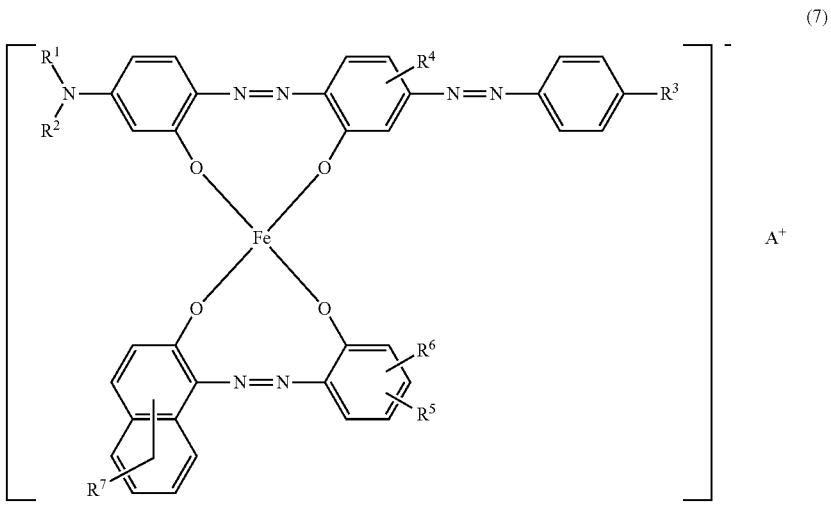

(7)

wherein, in the chemical formula (7), $R^1$-$R^7$ and $A^+$ are the same as ones of the chemical formula (1).

In the chemical formula (1), $R^4$ is a straight or branched alkyl group having 1-5 carbon atoms or a straight or branched alkoxy group having 1-5 carbon atoms. The alkyl group may include specifically a methyl group, an ethyl group, an n-propyl group, an isopropyl group, an n-butyl group, a sec-butyl group, a tert-butyl group, an n-pentyl group, an isopentyl group, and a neopentyl group, and the alkoxy group may include specifically a methoxy group, an ethoxy group, an n-propoxy group, an isopropoxy group, an n-butoxy group, a sec-butoxy group, a tert-butoxy group, an n-pentyloxy group, an isopentyloxy group, and a neopentyloxy group.

The disazo-monoazo iron complex is specifically represented by the following chemical formula (8):

[Chemical Formula 8]

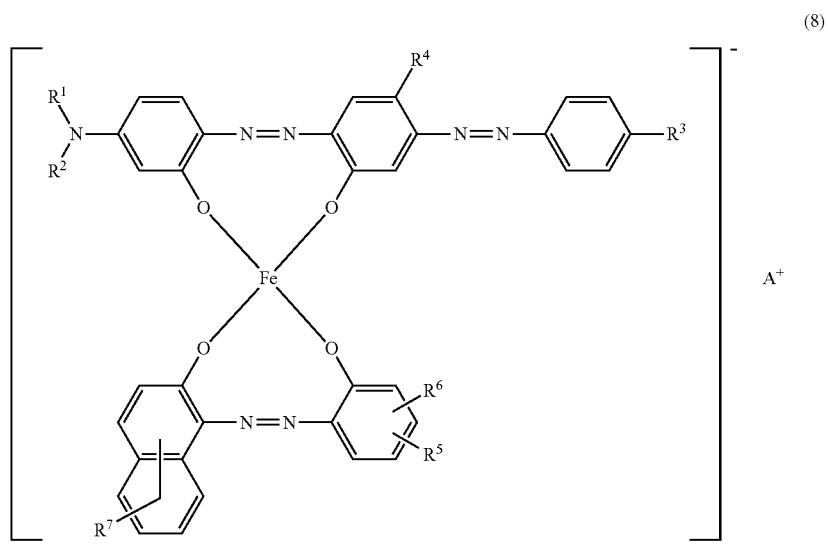

(8)

wherein, in the chemical formula (8), $R^1$-$R^7$ and $A^+$ are the same as ones of the chemical formula (1).

In the chemical formula (1), $R^5$ is a substituent having an electron-withdrawing group such as a nitro group, a sulfonamide group, or a halogen atom. The halogen atom may include fluorine, chlorine, bromine, and iodine. When R is bonded at the 4- or 5-position with respect to the azo group on the aromatic ring, it is preferable because it can further improve the blackness of the disazo-monoazo iron complex and hence achieve a sufficiently deep black for practical use.

In the chemical formula (1), $R^6$ is a hydrogen atom, a straight or branched alkyl group having 1-8 carbon atoms, a nitro group or a halogen atom. The alkyl group may include a methyl group, an ethyl group, an n-propyl group, an isopropyl group, an n-butyl group, an isobutyl group, a sec-butyl group, a tert-butyl group, an n-pentyl group, an isopentyl group, a neopentyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, a 2-methylheptyl group, a 3-methylheptyl group, a 4-methylheptyl group, a 2,2-dimethylhexyl group, a 2,3-dimethylhexyl group, a 2,4-dimethylhexyl group, a 2,5-dimethylhexyl group, a 3,3-dimethylhexyl group, a 3,4-dimethylhexyl group, a 2-ethylhexyl group, a 3-ethylhexyl group, a 2,2,3-trimethylpentyl group, a 2,2,4-trimethylpentyl group, a 2,3,3-trimethylpentyl group, a 2,3,4-trimethylpentyl group, a 2-methyl-3-ethylpentyl group, a 3-methyl-3-ethylpentyl group, and a 2,2,3,3-tetramethylbutyl group. The halogen atom may include fluorine, chlorine, bromine, and iodine.

The disazo-monoazo iron complex is specifically represented by the following chemical formula (9a):

[Chemical Formula 11]

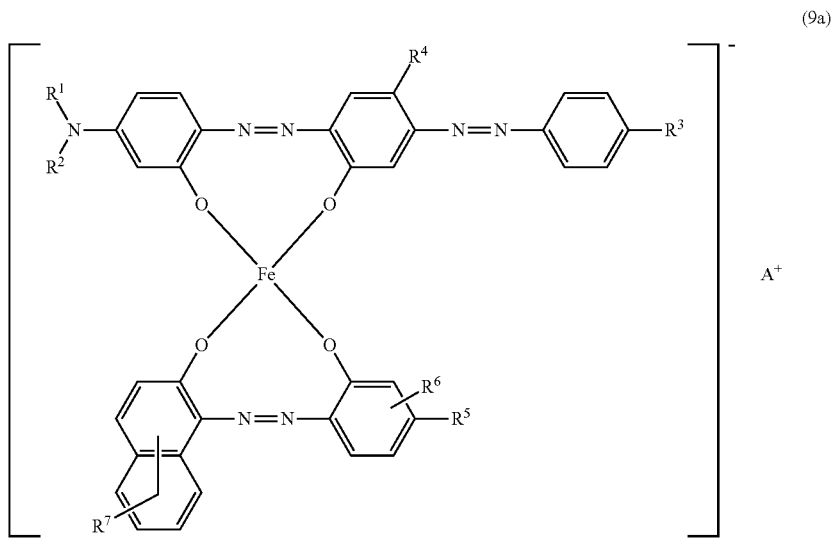

(9a)

wherein, in the chemical formula (9a), $R^1$-$R^7$ and $A^+$ are the same as ones of the chemical formula (1), and the chemical formula (9b):

[Chemical Formula 12]

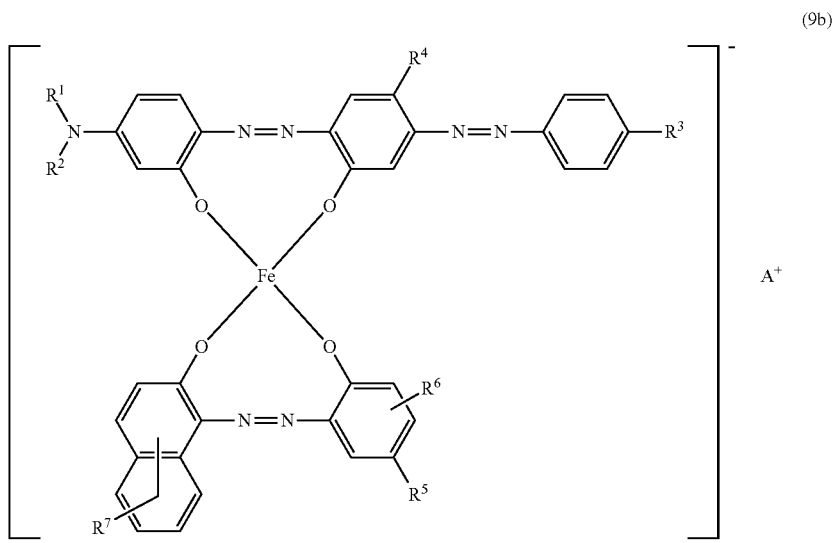

(9b)

wherein, in the chemical formula (9b). $R^1$-$R^7$ and $A^+$ are the same as ones of the chemical formula (1).

In the chemical formula (1), $R^7$ is a hydrogen atom or a straight or branched alkyl group having 3-12 carbon atoms. The alkyl group may include an n-propyl group, an isopropyl group, an n-butyl group, an isobutyl group, a sec-butyl group, a tert-butyl group, an n-pentyl group, an isopentyl group, a neopentyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, a tert-octyl group, a 2-methylheptyl group, a 3-methylheptyl group, a 4-methylheptyl group, a 2,2-dimethylhexyl group, a 2,3-dimethylhexyl group, a 2,4-dimethylhexyl group, a 2,5-dimethylhexyl group, a 3,3-dimethylhexyl group, a 3,4-dimethylhexyl group, a 2-ethylhexyl group, a 3-ethylhexyl group, a 2,2,3-trimethylpentyl group, a 2,2,4-trimethylpentyl group, a 2,3,3-trimethylpentyl group, a 2,3,4-trimethylpentyl group, a 2-methyl-3-ethylpentyl group, a 3-methyl-3-ethylpentyl group, a 2,2,3,3-tetramethylbutyl group, an n-nonyl group, an n-decyl group, a lauryl group, and a dodecyl group. Among these, a tert-butyl group, an isopentyl group, a hexyl group, an n-octyl group, a tert-octyl group, a 2-ethylhexyl group, an n-nonyl group, an n-decyl group, and a dodecyl group are preferable.

The disazo-monoazo iron complex is specifically represented by the following chemical formula (10a):

[Chemical Formula 13]

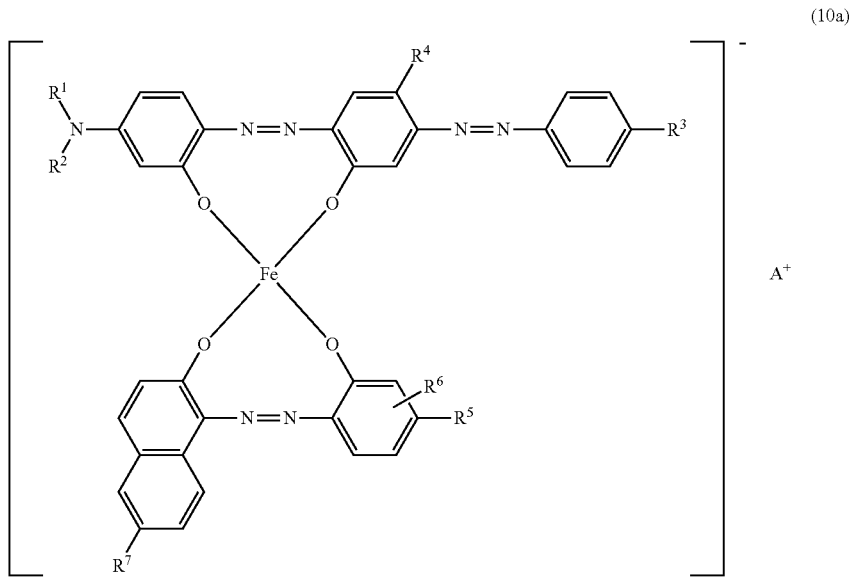

(10a)

wherein, in the chemical formula (10a), $R^1$-$R^7$ and $A^+$ are the same as ones of the chemical formula (1), the following chemical formula (10b):

[Chemical Formula 14]

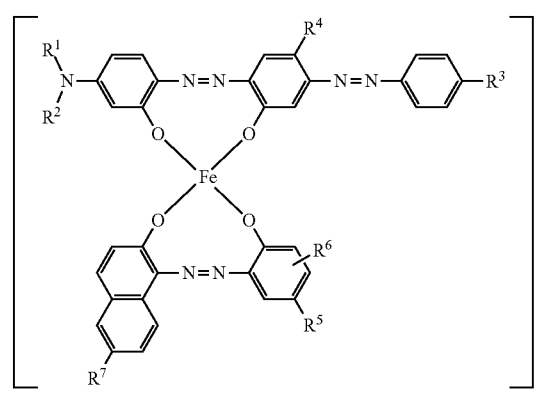

(10b)

wherein, in the chemical formula (10b), $R^1$-$R^7$ and $A^+$ are the same as ones of the chemical formula (1), the following chemical formula (10c):

[Chemical Formula 15]

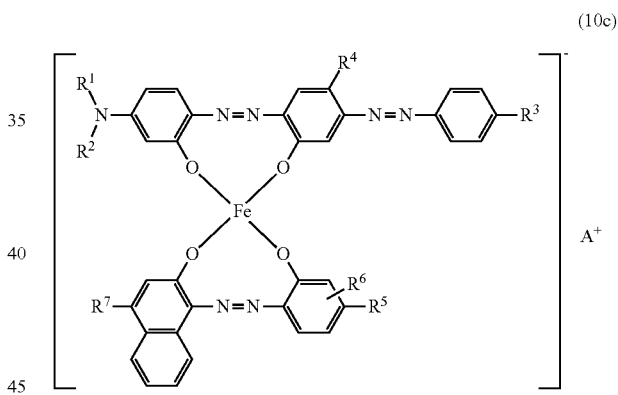

(10c)

wherein, in the chemical formula (10c). $R^1$-$R^7$ and $A^+$ are the same as ones of the chemical formula (1), and the following chemical formula (10d):

[Chemical Formula 16]

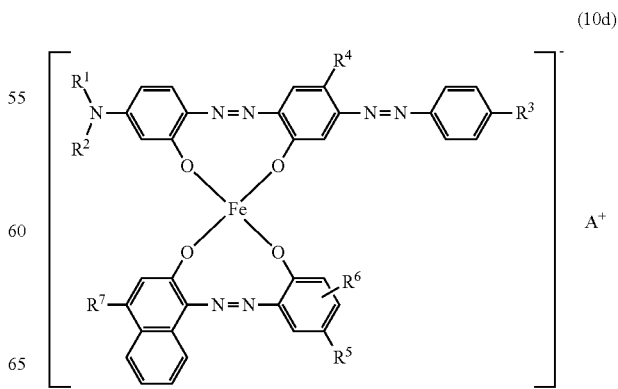

(10d)

wherein, in the chemical formula (10d), $R^1$-$R^7$ and $A^+$ are the same as ones of the chemical formula (1), In the chemical formula (1), $A^+$ is a monovalent cation. The monovalent cation may include a hydrogen ion, an alkali metal ion, an ammonium ion ($NH_4^+$), and a monovalent ammonium ion having an alkyl group. Among these monovalent cations, the disazo-monoazo iron complex may have only one kind of them or may have multiple kinds of them. In particular, the ammonium ion and the monovalent ammonium ion having an alkyl group are preferable. The alkali metal ion may include a lithium ion ($Li^+$), a sodium ion ($Na^+$), and a potassium ion ($K^+$). The alkali metal ion may be derived from a pH adjuster used in the process of synthesizing the disazo-monoazo iron complex. In addition, only one type or multiple types of the monovalent cation may be bonded to the iron complex anion.

The monovalent ammonium ion having an alkyl group is represented by the following chemical formula (4):

[Chemical Formula 17]

(4)

In the chemical formula (4), $R^8$ is a straight or branched alkyl group having 1-18 carbon atoms, and $R^9$ and $R^{10}$ are each independently a hydrogen atom or a straight or branched alkyl group having 1-8 carbon atoms. Those alkyl groups may include a methyl group, an ethyl group, an n-propyl group, an isopropyl group, an n-butyl group, a sec-butyl group, a tert-butyl group, an n-pentyl group, an isopentyl group, a neopentyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, a 2-methylheptyl group, a 3-methylheptyl group, a 4-methylheptyl group, a 2,2-dimethylhexyl group, a 2,3-dimethylhexyl group, a 2,4-dimethylhexyl group, a 2,5-dimethylhexyl group, a 3,3-dimethylhexyl group, a 3,4-dimethylhexyl group, a 2-ethylhexyl group, a 3-ethylhexyl group, a 2,2,3-trimethylpentyl group, a 2,2,4-trimethylpentyl group, a 2,3,3-trimethylpentyl group, a 2,3,4-trimethylpentyl group, a 2-methyl-3-ethylpentyl group, a 3-methyl-3-ethylpentyl group, a 2,2,3,3-tetramethylbutyl group, an n-nonyl group, an n-decyl group, an undecyl group, a lauryl group, and a stearyl group. Among these, a straight or branched alkyl group having 7-18 carbon atoms is preferable, a branched alkyl group having 8-15 carbon atoms is more preferable, and a branched alkyl group having 11-14 carbon atoms is much more preferable.

In the chemical formula (4), the alkyl groups of $R^9$ and $R^{10}$ may include specifically a methyl group, an ethyl group, an n-propyl group, an isopropyl group, an n-butyl group, an isobutyl group, a sec-butyl group, a tert-butyl group, an n-pentyl group, an isopentyl group, a neopentyl group, an n-hexyl group, an n-heptyl group, and an n-octyl group. Among these, a methyl group is preferable.

Since the disazo-monoazo iron complex essential to the azo iron complex dye of the present invention has an asymmetric structure containing a disazo ligand having an amino group (—$NR^1R^2$ in the chemical formula (1)) to which a dialkyl group having a specific range of carbon atoms is attached and an electron-withdrawing group (—$R^3$ in the same), and a monoazo ligand having an electron-withdrawing group (—$R^5$ and/or —$R^6$ in the same), the azo iron complex dye is bathochromic and absorbs wavelengths in the visible region, exhibiting a deep black color sufficient for practical use.

In addition, the aromatic ring of the disazo ligand is composed only of an arylene group, and does not have a bulky naphthalene ring that causes a high molecular weight. As a result, this azo iron complex dye has a low molecular weight compared to an azo iron complex dye with a naphthalene ring-containing disazo ligand, so that expresses high color development even in a small amount.

Furthermore, this disazo-monoazo iron complex contains an alkaline metal ion, an ammonium ion, and/or an ammonium ion with a monovalent alkyl group containing an alkyl group having a specific range of carbon atoms as cations, so the solubility of the black azo iron complex anion is improved. As a result, the azo iron complex dye of the present invention exhibits a higher practical solubility as an ink composition in organic solvents including an alcoholic organic solvent such as ethanol and ethylene glycol and a ketone-based organic solvent such as methyl ethyl ketone, and does not deposit or precipitate in organic solvents due to its high dissolution stability. Thus, this azo iron complex dye is suitable for the ink composition, in particular, for the ink composition for a continuous-type ink-jet (CIJ) printer. In addition, since the azo iron complex dye does not contain heavy metals chromium or cobalt which are harmful to the environment and the human body, it can contribute to environmental conservation and ensure safety to the human body.

The azo iron complex dye of the present invention further contains preferably the monoazo-monoazo iron complex having only a monoazo ligand that is a ligand of the disazo-monoazo iron complex and/or further the disazo-disazo iron complex having only a disazo ligand in addition to the disazo-monoazo iron complex represented by the chemical formula (1).

The monoazo-monoazo iron complex is represented by the following chemical formula (2):

[Chemical Formula 18]

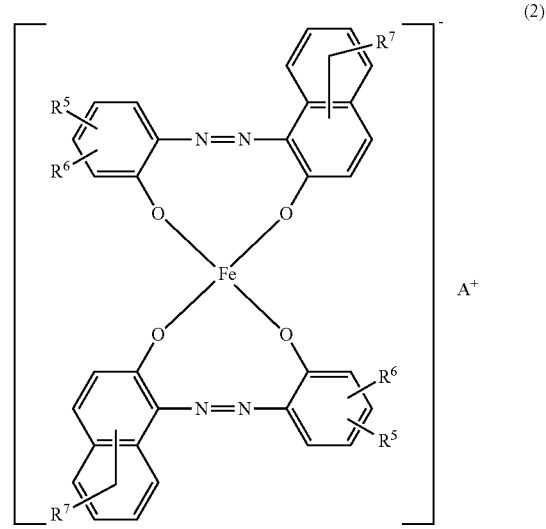

(2)

wherein, in the chemical formula (2). $R^5$-$R^7$ and $A^+$ are the same as ones of the chemical formula (1).

In addition, the disazo-disazo iron complex is represented by the following chemical formula (3):

[Chemical Formula 19]

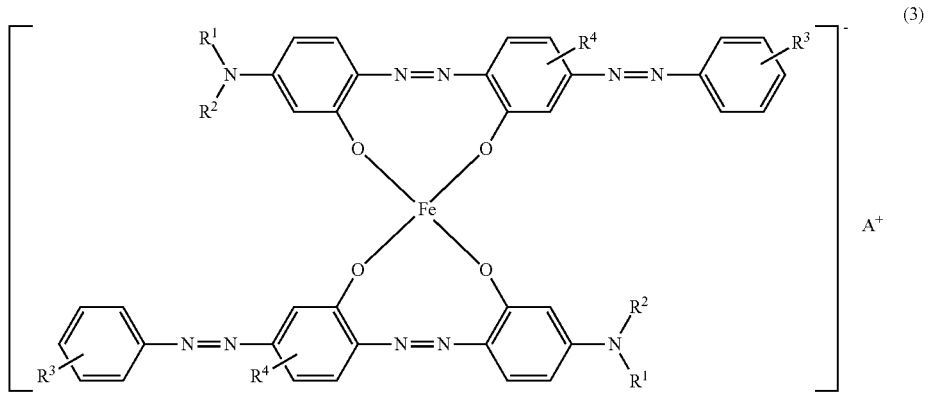

(3)

wherein, in the chemical formula (3), $R^1$-$R^4$ and $A^+$ are the same as ones of the chemical formula (1).

When the azo iron complex dye contains a disazo-monoazo iron complex (DM-form), a monoazo-monoazo iron complex (MM-form) and a disazo-disazo iron complex (DD-form), these molar ratios can be expressed as peak area ratios in the chromatogram obtained by measuring them through high performance liquid chromatography at a specific wavelength, for example at a wavelength of 254 nm. Specifically, the DM-form:MM-form:DD-form=20-70:5-80:0-50 is preferable, 20-65:5-80:0-50 is more preferable, 20-60:20-80:0-30 is much more preferable, and 20-55:20-80:0-15 is most preferable. In addition, the lower limit of the DD-form may be 1 instead of above 0. Note that the above values are calculated up by rounding off the peak area ratio to one decimal place, and, for example, the notation of 0, which is the lower limit of the D-form, includes values of 0.1 to 0.4, which are values exceeding 0.0.

When the azo iron complex dye contains additionally a symmetrical azo iron complex dye such as a monoazo-monoazo iron complex having only a monoazo ligand and/or a disazo-disazo iron complex having only a disazo ligand in addition to an asymmetric azo iron complex such as a disazo-monoazo iron complex, by virtue of setting the ratio of each azo iron complex in the azo iron complex to an appropriate range, it is preferable that blackness, solubility, and dissolution stability of the azo iron complex dye, and further electrical conductivity required for the ink composition for a continuous-type ink-jet (CIJ) printer can be adjusted appropriately and arbitrarily.

The azo iron complex dye of the present invention can be suitably used in the ink composition for a CIJ printer. Herein, the electrical conductivity K of the azo iron complex dye is preferably 300-2200 μS/cm, and more preferably 600-2000 μS/cm. As long as the electrical conductivity is within this range, the charge of the ink composition for a CIJ printer containing the azo iron complex dye can be stably and freely controlled, so that the ejection stability of the ink composition can be improved. Note that the electrical conductivity K is measured by inserting and immersing an electrode of an electrical conductivity meter in a 6 mass % methyl ethyl ketone solution of the azo iron complex dye.

The alkaline metal ion content of the azo iron complex dye is preferably 1000 ppm or less, and more preferably 500 ppm or less. As a result, the surface tension of the ink composition can be lowered, so that the ink composition can be suitably used for a CIJ printer.

The additives such as a leveling agent and an anti-repellent agent contained in the ink composition for the CIJ printer may have silicone compounds or silicone-based surfactants. However, when the metal ion content in the azo iron complex dye is within the above range, the complex formation between these silicone compounds or silicone-based surfactants and alkaline metal ions can be suppressed. As a result, the clogging of a printer head is prevented and the ejection stability of the ink composition for the CHI printer is improved.

To obtain the azo iron complex dyes having the azo iron complex represented by the chemical formulas (1)-(3), it is preferable to adopt a producing method composed of the 1st step to 5th step as follows.

The 1st step: Step for obtaining disazo dye using diazo coupling reaction

The 2nd step: Step for obtaining monoazo dye using diazo coupling reaction

The 3rd step: Step for obtaining azo iron complex dye by iron-complexation of a mixture of disazo dye and monoazo dye The 4th step: Step for altering and preparing cation of azo iron complex dye The 5th step: Step for filtering, cleaning, drying, and crushing azo iron complex dye According to the producing method, a high purity of the azo iron complex dye can be obtained. Each step will be described in detail below.

The 1st Step: Step for Obtaining Disazo Dye Using Diazo Coupling Reaction

The 1st step is a step to obtain the disazo dye that can serve as a disazo ligand in the azo iron complex.

(1-1: Preparation of Monoazo Compound)

Firstly, as shown in the following chemical formula (11), diazotization of a specific aromatic amine by the known method, and then a diazo coupling reaction is performed with 2-aminophenol by a conventional method gives the monoazo compound as an intermediate of the disazo dye.

[Chemical Formula 20]

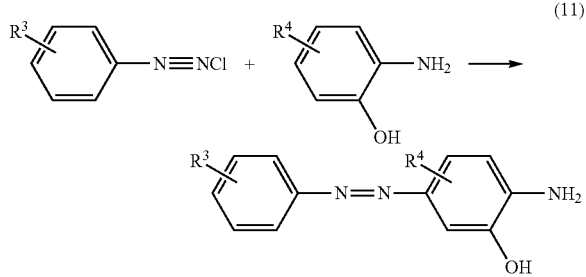

(11)

wherein, in the chemical formula (11), $R^3$ and $R^4$ are the same as ones of the chemical formula (1).

In the reaction of the chemical formula (11), specifically, for example, an aqueous solution prepared by diluting an aminobenzene (diazo component) having an electron-withdrawing substituent with hydrochloric acid and sodium nitrite (for example, 40 mass % prepared aqueous solution) are added to an ion-exchanged water or an ion-exchanged water-lower alcohol mixed solvent, and then the aminobenzene is diazotized at 0-5° C. by stirring for 1-3 hours to give the diazotization solution. Excess sodium nitrite is decomposed with sulfamic acid, or the like.

Next, after an aminophenol having a substituent like a hydroxyl group suitable for forming metal complex salts is dissolved or finely dispersed in an aqueous solution diluted with hydrochloric acid, to this solution is added dropwise the diazotization solution, and a diazo coupling reaction is performed in a hydrophilic solvent or in a water-lower alcoholic solvent at room temperature or at low temperature by stirring for a couple of hours to give a solution containing the monoazo compound. The monoazo compound is filtered and washed with water to obtain a wet cake of the monoazo compound. In the next step of synthesizing the disazo dye, the wet cake can be used after drying, the wet cake can be used as it is, or the monoazo compound-containing solution can be used as it is.

(1-2: Preparation of Disazo Dye)

The monoazo compound obtained in the above synthesis is diazotized by the known method as shown in the following chemical formula (12), and then a diazo coupling reaction is performed with an aminophenol compound having specific alkyl amino groups to give a solution containing the disazo dye.

[Chemical Formula 21]

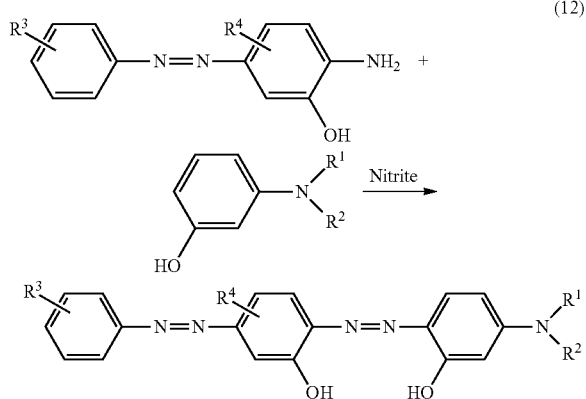

(12)

wherein, in the chemical formula (12), $R^1$-$R^4$ are the same as ones of the chemical formula (1).

In the reaction of the chemical formula (12), specifically, for example, an aqueous solution prepared by diluting the monoazo compound obtained in the above monoazo compound synthesis with hydrochloric acid and sodium nitrite (for example, 40 mass % prepared aqueous solution) are added to an ion-exchanged water or an ion-exchanged water-lower alcohol mixed solvent, and then the aminobenzene is diazotized at 0-5° C. by stirring for 1-3 hours to give the diazotization solution. Excess sodium nitrite is decomposed with sulfamic acid, or the like.

Next, after an aminophenol having a substituent like a hydroxyl group suitable for forming metal complex salts is dissolved or finely dispersed in an aqueous alkaline solution, to this solution is added dropwise the diazotization solution, and a diazo coupling reaction is performed in a hydrophilic solvent or in a water-lower alcoholic solvent at room temperature or at low temperature by stirring for a couple of hours to give a solution containing the disazo dye. The disazo dye is filtered and washed with water to obtain a wet cake of the disazo dye. In a later step for iron-complexation, the wet cake can be used after drying, the wet cake can be used as it is, or the disazo dye-containing solution can be used as it is.

The 2nd Step: Step for Obtaining Monoazo Dye Using Diazo Coupling Reaction

The 2nd step is a step to obtain the monoazo dye that can serve as a monoazo ligand in the azo iron complex.

Firstly, diazotization of an aromatic amine having an electron-withdrawing group such as a nitro group and a halogen atom by the known method gives the diazotization solution. Specifically, for example, an aqueous solution prepared by diluting an aminobenzene (diazo component) having an electron-withdrawing substituent with hydrochloric acid and sodium nitrite (for example, 40 mass % prepared aqueous solution) are added to an ion-exchanged water or an ion-exchanged water-lower alcohol mixed solvent, and then the aminobenzene is diazotized at 0-5° C. by stirring for 1-3 hours to give the diazotization solution. Excess sodium nitrite is decomposed with sulfamic acid, or the like.

Next, as shown in the following chemical formula (13), the diazocoupling reaction of the diazo compound in the diazotization solution obtained by the above with 2-naphthol by the known method gives the monoazo dye.

[Chemical Formula 22]

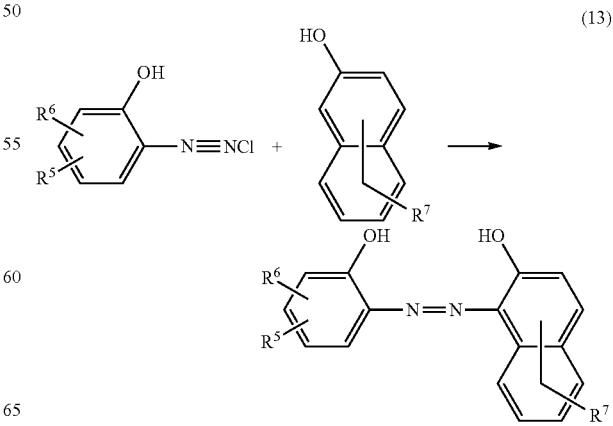

(13)

wherein, in the chemical formula (13), $R^5$-$R^7$ are the same as ones of the chemical formula (1).

The reaction shown in the chemical formula (13) is specifically performed as follows. 2-Naphthol is dissolved or finely dispersed in an aqueous alkaline solution, and then to this solution is added dropwise the diazotization solution, and a diazo coupling reaction is performed in a hydrophilic solvent or in a water-lower alcoholic solvent at room temperature or at low temperature by stirring for a couple of hours to give a solution containing the monoazo dye. The monoazo dye is filtered and washed with water to obtain a wet cake of the monoazo dye. In a later step for iron-complexation, the wet cake can be used after drying, the wet cake can be used as it is, or the monoazo dye-containing solution can be used as it is.

The 3rd Step: Step for Obtaining Azo Iron Complex Dye by Iron-Complexation of a Mixture of Disazo Dye and Monoazo Dye The 3rd step is an iron-complexation step to perform an iron-complexation in which the disazo dye obtained in the above step is ironized with the monoazo dye to give the azo iron complex (the azo iron complex anion).

The disazo dye obtained in the 1st step and the monoazo dye obtained in the 2nd step are prepared, for example, in a molar ratio of 2:8 and mixed to obtain a mixed dye. The mixed dye is dispersed or dissolved in a solvent and, after addition of an ironizing agent, heated and stirred at 80-140° C. for 1-5 hours. Through this process, as shown in the following chemical formula (14), the ironization reaction proceeds, and the disazo dye and the monoazo dye are coordinated to the iron atom to give a mixture of the disazo-monoazo iron complex shown in the chemical formula (1), the monoazo-monoazo iron complex shown in the chemical formula (2), and the disazo-disazo iron complex shown in the chemical formula (3).

[Chemical Formula 23]

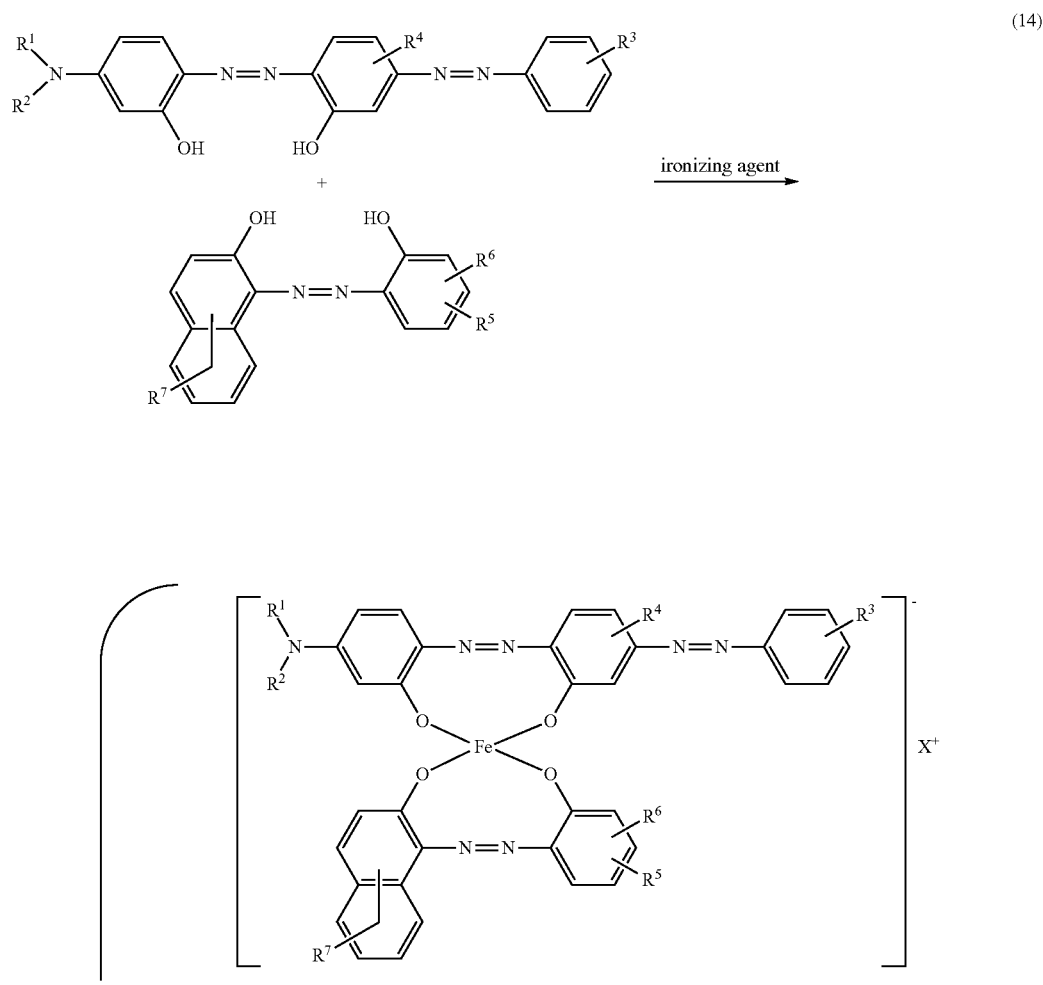

-continued

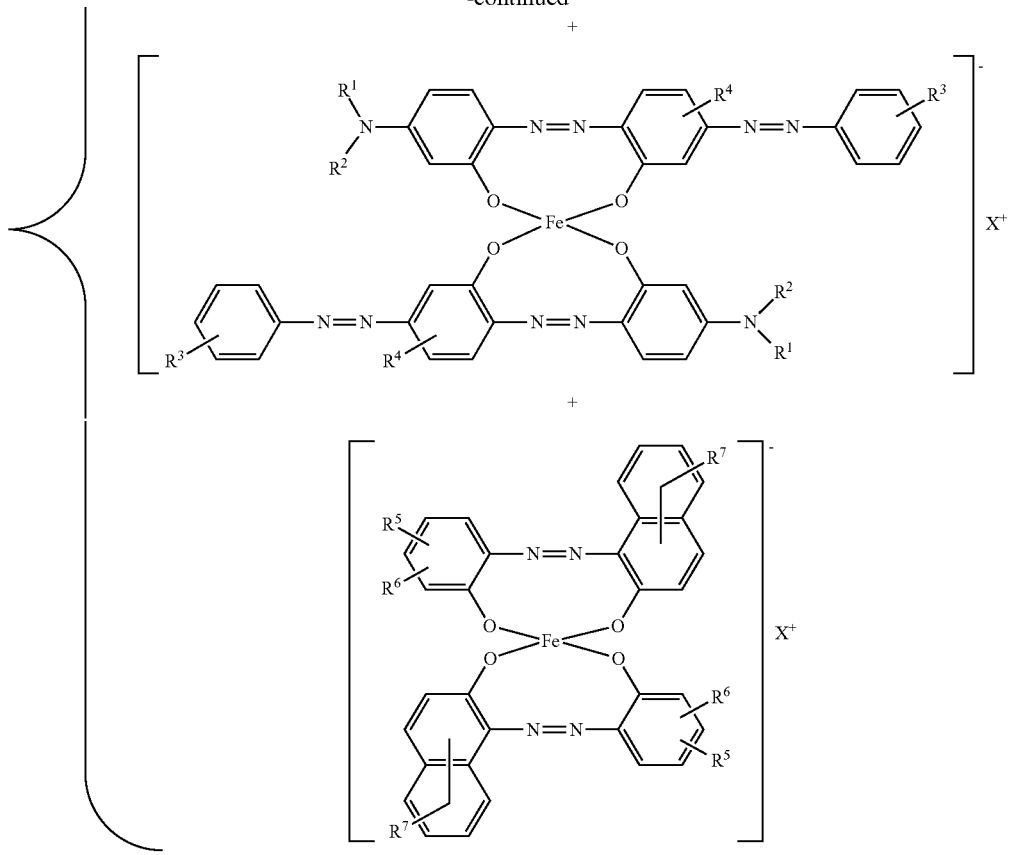

wherein, in the chemical formula (14), $R^1$-$R^7$ are the same as ones of the chemical formula (1) and $X^+$ is any cation.

The mixing ratio of the disazo dye and the monoazo dye is preferably 2:8 to 8:2 in terms of molar ratio. Specifically, the mixing ratios of 2:8, 3:7, 4:6, 5:5, 6:4, 7:3, and 8:2 are exemplified. In particular, when the disazo dye:the monoazo dye ratios are 2:8 to 5:5, it is preferred to exhibit high blackness and high solubility in an organic solvent contained in the ink composition.

The solvent used in the iron-complexation step may include a water, a water-organic solvent mixed solution, and an organic solvent, and, in particular, a water-organic solvent mixed solvent is preferred. The organic solvent may include alcoholic solvents, glycolic solvents, amide solvents, ethereal solvents, ketone-based solvents, sulfoxide solvents, and aromatic hydrocarbon solvents and, in particular, alcoholic solvents, glycolic solvents, amide solvents, and sulfoxide solvents are preferred.

The preferred organic solvent may include specifically an alcoholic solvent such as ethanol, n-propanol, isopropanol, n-butanol, isobutanol, amyl alcohol, benzyl alcohol, cyclohexanol, and diacetone alcohol; an alkyl ether of glycols such as ethylene glycol monomethyl ether, ethylene glycol monoethyl ether, propylene glycol monomethyl ether, propylene glycol monoethyl ether, diethylene glycol monoethyl ether, diethylene glycol monobutyl ether, and propylene glycol monoethyl ether; an acetate of glycols such as ethylene glycol monoacetate and propylene glycol monoacetate; a glycolic solvent such as glycols including ethylene glycol, diethylene glycol, trimethylene glycol, triethylene glycol, tetraethylene glycol, polyethylene glycol, propylene glycol, and butanediol; an amide solvent such as N-methylformamide, N,N-dimethylformamide, N-ethylformamide, N,N-diethylformamide, N-methylacetamide, and N,N-dimethylacetamide. A sulfoxide solvent may include sulfolane, 3-methylsulfolane, and dimethylsulfoxide. Among these, an amide solvent is preferred.

The ironizing agent used in the iron-complexation step may include ferric sulfate, ferrous sulfate, ferric chloride, ferrous chloride, ferric nitrate, iron acetate, and iron lactate. The amount of the ironizing agent is preferably such that the number of equivalents of the ironizing agent is preferably ½ to 2, and more preferably ½ to ⅔, with respect to the total number of equivalents of the disazo dye and the monoazo dye. Further, the ironization reaction is preferably carried out at a temperature suitable for the type of solvent used while heating (including stirring under reflux). The ironization reaction may be carried out with the addition of additives such as a reaction accelerator and a pH adjuster. By adjusting the pH by adding an acid or base, the desired cation $A^+$, for example, a hydrogen ion, a sodium ion, a potassium ion, an ammonium ion, a monovalent ammonium ion having an alkyl group, or mixtures thereof, can be prepared from any cation $X^+$ combined with the azo iron complex anion during the course of the reaction.

In the 3rd step, the ironization reaction after mixing the disazo dye obtained in the 1st step with the monoazo dye obtained in the 2nd step is exemplified, but the 3rd step is not limited to this, and the disazo dye or the monoazo dye may be added to the solvent, then the monoazo dye or the disazo dye may be sequentially added, and the ironizing agent may be added to cause ironization with the trivalent iron. And also the disazo dye or the monoazo dye may be added to the solvent, then the ironizing agent may be added to cause ironization, and thereafter the monoazo dye or the disazo dye may be added, and, if necessary, the ironizing agent may be added further to cause ironization with the trivalent iron. In this case, the disazo-monoazo iron complex is formed by the ironization reaction between an excess of the azo dye that has undergone the ironization reaction first and another azo dye that was added later.

In addition, each of the disazo dye and the monoazo dye may be used singly or by mixing multiple types having different substituents or different positions of the substituents. For example, this may include that one disazo dye can be mixed with two monoazo dyes, or two disazo dyes can be mixed with one monoazo dye.

The 4th Step: Step for Altering and Preparing Cation of Azo Iron Complex Dye

The 4th step is a step for altering and preparing the cation of the azo iron complex dye. Thus, this is an ion-exchange step that uses an alkali metal solution, an aqueous ammonium solution, and/or a monovalent amine having an alkyl group with 3-18 carbon atoms to cause iron-complexation of a mixture of the azo dyes and to exchange the cation of the azo iron complex dye that is obtained in the process for preparing the azo iron complex dye for the desired cation.

For example, when a cation of the azo iron complex dye obtained in the above step is a hydrogen ion or alkaline metal ion, these cations are exchanged by an ammoniation agent. By this cation-exchange reaction, the azo iron complex dye into which the ammonium cation is introduced is obtained as shown in the following chemical formula (15).

[Chemical Formula 24]

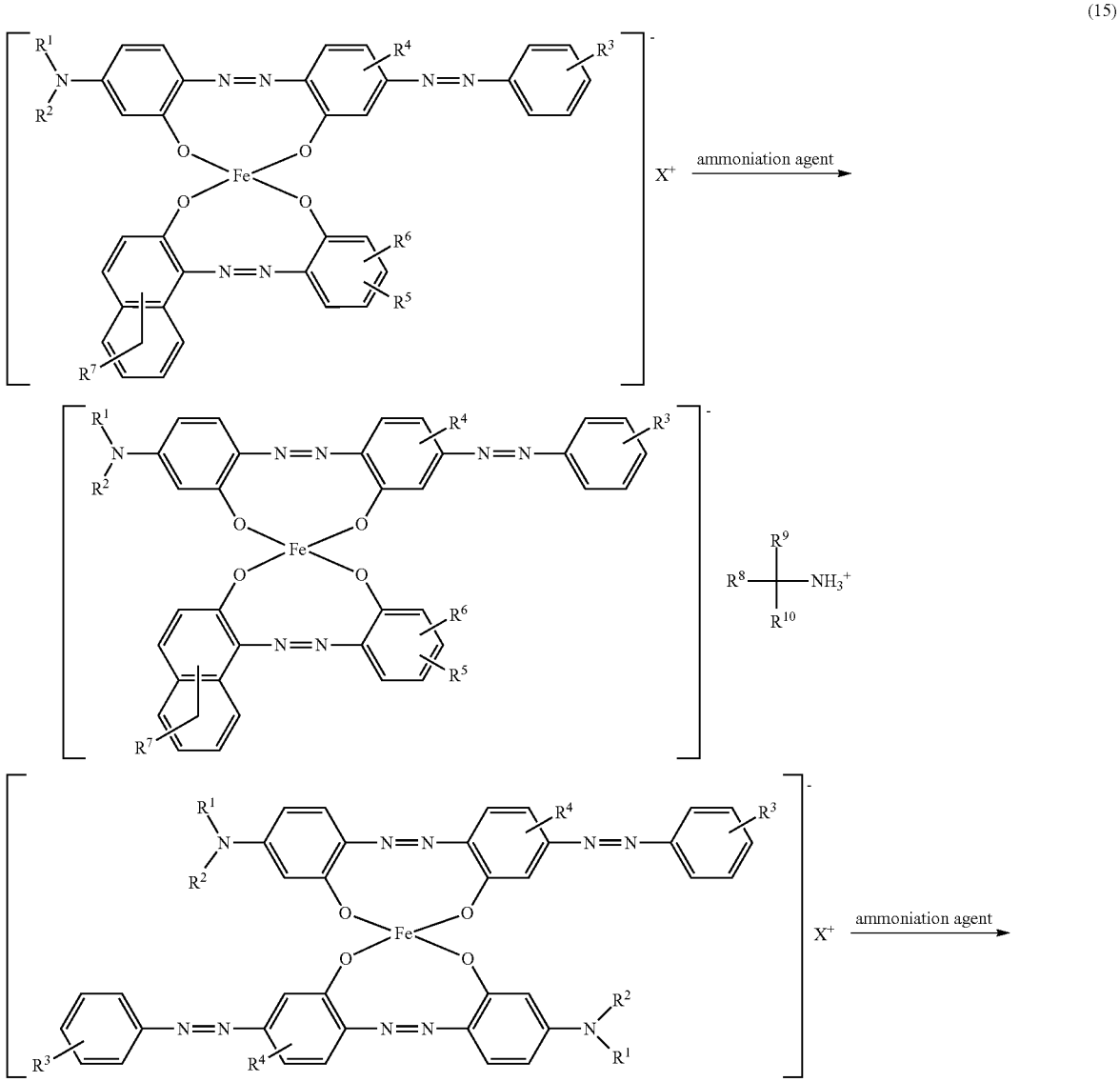

(15)

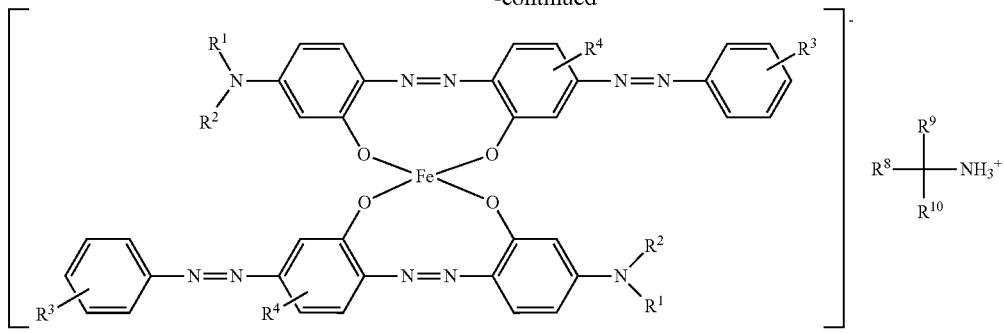

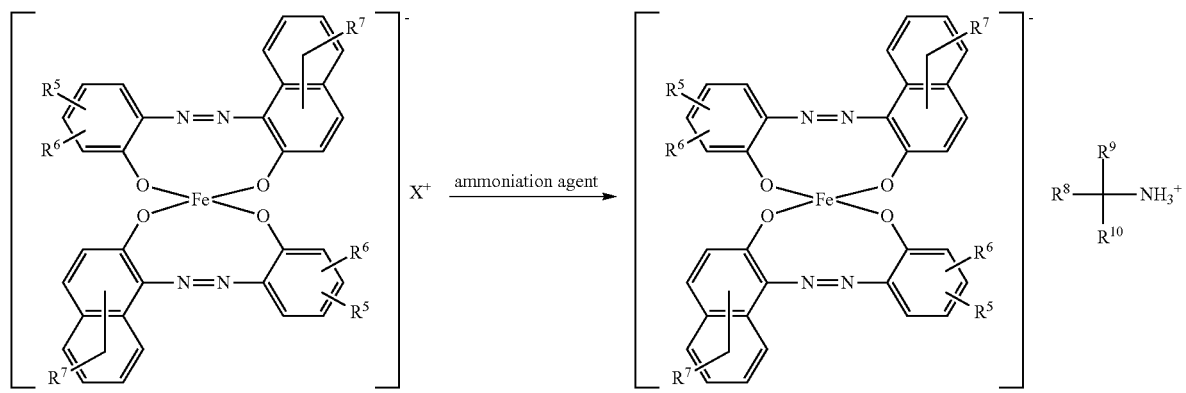

wherein, in the chemical formula (15), $R^1$-$R^7$ are the same as ones of the chemical formula (1). $R^8$-$R^{10}$ are the same as ones of the chemical formula (4), and $X^+$ is any cation.

The ammoniation agent may include an aqueous ammonium solution and a monovalent amine compound having an alkyl group with 3-18 carbon atoms. The ammoniation agent may be used singly or by mixing multiple types.

By combining each condition such as the amount of an acid, a base and an ammoniation agent used in the cation-exchange and a reaction temperature, the azo iron complex having a mixed ion as a cation is obtained. Thus, it is possible to obtain the azo iron complex in which 86 mol % or more, in particular, 90 mol % or more of the cation in the mixed ion are the desired ammonium ion.

The cation-exchange reaction in the 4th step can be carried out simultaneously or sequentially in the same reaction system as the ironization reaction in the 3rd step. In addition, the 4th step may be performed by adding an ammoniation agent together with an organic solvent when preparing the ink composition.

The 5th Step: Step for Filtering, Cleaning, Drying, and Crushing Azo Iron Complex Dye The 5th step, if necessary, is performed after the 3rd or the 4th step, and optionally comprises filtering, washing, drying, and grinding steps.

The filtering step is a step of separating the reaction solution containing the azo iron complex dye obtained by the iron-complexation step as the 3rd step (or subsequent alkaline treatment) or by the ion-exchange step into a solid matter of the azo iron complex dye and the solvent by filtration to obtain a wet cake of the azo iron complex dye. A filtration technique may include a gravity filtration technique such as a filter paper filtration, a bag filtration, and centrifugation; a vacuum filtration technique using filters such as Nutsche, Moor filter, Disc filter, Drum filter, and Oliver filter; a pressure filtration technique such as a filter press, a closed leaf filter, and a closed multi-stage filter.

After the filtering step, a washing step may be performed. Thus, the azo iron complex or the wet cake of the azo iron complex or the azo iron complex dye is thoroughly washed with a washing solution. The washing solution may include water and an organic solvent, but water is preferred. The wet cake may be used as it is as an intermediate in the next step.

After the washing step, a drying step may be performed to dry the wet cake of the azo iron complex dye. If necessary, the additional drying step may be performed. The dried bulk azo iron complex dye is crushed or pulverized using a known pulverizer so as to have a desired particle size.

For the azo iron complex dye of the present invention, the following details the specific examples of a disazo ligand and a monoazo ligand possessed by the disazo-monoazo iron complex (DM-form), the monoazo-monoazo iron complex (MM-form), and the disazo-disazo iron complex (DD-form), respectively, and also the azo iron complex dye in which those ligands are combined.

(Disazo Ligand)

The disazo ligand (D-ligand) that is a ligand of the azo iron complex dye of the present invention is specifically represented by the following chemical formula (16).

[Chemical Formula 25]

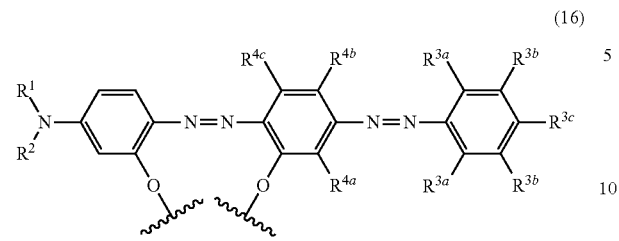

(16)

wherein, in the chemical formula (16), $R^1$ and $R^2$ are the same as ones of the chemical formula (1); any one of $R^{3a}$-$R^{3c}$ is an electron-withdrawing group selected from the group consisting of a cyano group, a nitro group, an acetyl group, a sulfonamide group, and a halogen atom, and others are hydrogen atoms; any one of $R^{4a}$-$R^{4c}$ is a straight or branched alkyl group having 1-5 carbon atoms or a straight or branched alkoxy group having 1-5 carbon atoms, and others are hydrogen atoms.

In the chemical formula (16), the specific substituents of $R^1$, $R^2$, $R^{3a}$-$R^{3c}$, and $R^{4a}$-$R^{4c}$ are shown in Table 1.

TABLE 1

| D Ligand | $R^1$ | $R^2$ | $R^{3a}$ | $R^{3b}$ | $R^{3c}$ | $R^{4a}$ | $R^{4b}$ | $R^{4c}$ |
|---|---|---|---|---|---|---|---|---|
| D1 | n-$C_4H_9$ | n-$C_4H_9$ | H | H | CN | H | $CH_3$ | H |
| D2 | n-$C_4H_9$ | n-$C_4H_9$ | H | H | $NO_2$ | H | $CH_3$ | H |
| D3 | n-$C_4H_9$ | n-$C_4H_9$ | H | H | $COCH_3$ | H | $CH_3$ | H |
| D4 | n-$C_4H_9$ | n-$C_4H_9$ | H | H | $SO_2NH_2$ | H | $CH_3$ | H |
| D5 | tert-$C_4H_9$ | tert-$C_4H_9$ | H | H | CN | H | $CH_3$ | H |
| D6 | iso-$C_3H_7$ | iso-$C_3H_7$ | H | H | CN | H | $CH_3$ | H |
| D7 | tert-$C_3H_{17}$ | tert-$C_8H_{17}$ | H | CN | H | H | $OCH_3$ | H |
| D8 | sec-$C_4H_9$ | sec-$C_1H_9$ | H | H | $NO_2$ | H | $C_2H_5$ | H |
| D9 | iso-$C_3H_7$ | iso-$C_3H_7$ | H | H | CN | H | $OCH_3$ | H |
| D10 | n-$C_4H_9$ | n-$C_4H_9$ | H | $COCH_3$ | H | H | $C_2H_5$ | H |
| D11 | 2-EtHx | 2-EtHx | H | H | $SO_2NH_2$ | H | $CH_3$ | H |
| D12 | n-$C_4H_9$ | n-$C_4H_9$ | H | H | CN | H | $OCH_3$ | H |
| D13 | n-$C_4H_9$ | n-$C_4H_9$ | H | CN | H | H | $OCH_3$ | H |
| D14 | iso-$C_5H_{11}$ | iso-$C_5H_{11}$ | H | H | $COCH_3$ | H | $C_3H_7$ | H |
| D15 | n-$C_4H_9$ | n-$C_4H_9$ | H | H | $C_1$ | H | $OC_2H_5$ | H |
| D16 | n-$C_4H_9$ | n-$C_4H_9$ | $NO_2$ | H | H | H | $CH_3$ | H |
| D17 | iso-$C_3H_7$ | iso-$C_3H_7$ | H | H | $SO_2NH_2$ | H | $C_2H_5$ | H |
| D18 | 2-EtHx | 2-EtHx | H | CN | H | H | $OCH_3$ | H |
| D19 | n-$C_4H_9$ | n-$C_4H_9$ | H | $NO_2$ | H | H | $OCH_3$ | H |
| D20 | tert-$C_3H_{17}$ | tert-$C_8H_7$ | H | $COCH_3$ | H | H | $CH_3$ | H |

(Monoazo Ligand)

The monoazo ligand (M ligand) that is a ligand of the azo iron complex dye of the present invention is specifically represented by the following chemical formula (17).

[Chemical Formula 26]

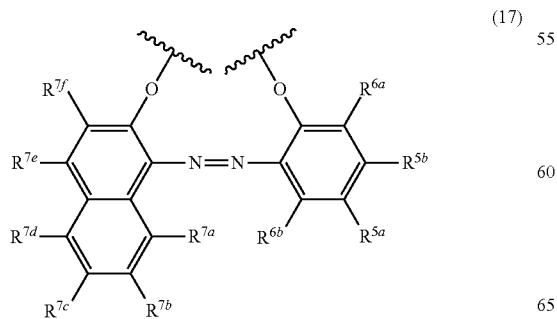

(17)

wherein, in the chemical formula (17), $R^{5a}$ and $R^{5b}$ are each independently a hydrogen atom, a nitro group, a sulfonamide group, or a halogen atom; $R^{6a}$ and $R^{6b}$ are each independently a hydrogen atom, a straight or branched alkyl group having 1-8 carbon atoms, a nitro group, or a halogen atom; $R^{7a}$-$R^{7f}$ are each independently a hydrogen atom or a straight or branched alkyl group having 3-12 carbon atoms. Herein, it is preferred that not all of $R^{5a}$, $R^{5b}$, $R^{6a}$ and $R^{6b}$ are the same substituent at the same time, and it is preferred that any one of $R^{7a}$-$R^{7f}$ is an alkyl group and the others are all hydrogen atoms.

Specific substituents of $R^{5a}$, $R^{5b}$, $R^{6a}$, $R^{6b}$, and $R^{7a}$-$R^{7f}$ in the chemical formula (17) are shown in Table 2.

TABLE 2

| M Ligand | $R^{5a}$ | $R^{5b}$ | $R^{6a}$ | $R^{6b}$ | $R^{7a}$ | $R^{7b}$ | $R^{7c}$ | $R^{7d}$ | $R^{7e}$ | $R^{7f}$ |
|---|---|---|---|---|---|---|---|---|---|---|
| M1  | $NO_2$      | H           | H   | H           | H | H | H            | H | H | H |
| M2  | H           | $NO_2$      | H   | $NO_2$      | H | H | H            | H | H | H |
| M3  | tert-$C_4H_9$ | $NO_2$    | H   | $NO_2$      | H | H | H            | H | H | H |
| M4  | Cl          | H           | H   | H           | H | H | H            | H | H | H |
| M5  | H           | Br          | H   | Br          | H | H | H            | H | H | H |
| M6  | $NO_2$      | tert-$C_3H_{17}$ | H | tert-$C_8H_{17}$ | H | H | H      | H | H | H |
| M7  | iso-$C_5H_{11}$ | H       | $NO_2$ | H        | H | H | H            | H | H | H |
| M8  | Cl          | H           | Cl  | H           | H | H | H            | H | H | H |
| M9  | $NO_2$      | H           | Cl  | H           | H | H | H            | H | H | H |
| M10 | $NO_2$      | H           | $NO_2$ | H        | H | H | H            | H | H | H |
| M11 | tert-$C_4H_9$ | $NO_2$    | H   | H           | H | H | H            | H | H | H |
| M12 | Cl          | H           | H   | H           | H | H | tert-$C_8H_{17}$ | H | H | H |
| M13 | $NO_2$      | H           | H   | H           | H | H | tert-$C_4H_9$ | H | H | H |
| M14 | H           | $NO_2$      | H   | H           | H | H | H            | H | n-$C_3H_7$ | H |
| M15 | H           | Cl          | H   | H           | H | H | H            | H | n-$C_3H_7$ | H |
| M16 | H           | $SO_2NH_2$  | H   | H           | H | H | H            | H | H | H |

The azo iron complex dye of the present invention contains at least the disazo-monoazo iron complex (DM-form), in which one mol each of at least one kind of the disazo ligand (D-ligand) represented by the above chemical formula (16) and specifically, for example, having a substituent shown in Table 1 and at least one kind of the monoazo ligand (M-ligand) represented by the above chemical formula (17) and specifically, for example, having a substituent shown in Table 2, are coordinated to an iron atom.

In addition to the DM-form, the azo iron complex dye may further contain the monoazo-monoazo iron complex (MM-form) in which 2 mol of one kind of the M-ligand represented by the above chemical formula (17) and specifically, for example, shown in Table 2 is coordinated to one mol of an iron atom, and the disazo-disazo iron complex (DD-form) in which 2 mol of at least one kind of the D-ligand represented by the above chemical formula (16) and specifically, for example, having a substituent shown in Table 1 is coordinated to one mol of an iron atom. In the azo iron complex dye, the ratio of each azo iron complex species, the D-ligand species and the M-ligand species they have, and the charging mixing ratio of the disazo dye (D-dye) and the monoazo dye (M-dye) for obtaining each azo iron complex dye are shown in Table 3. Note that in Table 3 the symbols in the D-ligand and the M-ligand columns correspond to the descriptions in Tables 1 and 2.

TABLE 3

| Azo iron complex dye | D ligand | M ligand 1 | M ligand 2 | D dye/M dye 1/M dye 2 Charging mixing ratio (molar ratio) | DM form/MM form/DD form HPLC peak area ratio |
|---|---|---|---|---|---|
| 1  | D1  | M1 | —  | 2.5/7.5/0 | 40/59/1 |
| 2  | D2  | M2 | —  | 3/7/0     | 57/40/3 |
| 3  | D3  | M3 | —  | 4/6/0     | 51/46/3 |
| 4  | D4  | M1 | —  | 2/8/0     | 58/33/9 |
| 5  | D1  | M2 | —  | 5/5/0     | 61/21/18 |
| 6  | D2  | M1 | —  | 2/8/0     | 21/78/1 |
| 7  | D4  | M2 | —  | 4/6/0     | 44/48/8 |
| 8  | D1  | M1 | M2 | 2/4/4     | 30/69/1 |
| 9  | D1  | M4 | —  | 2/8/0     | 22/76/2 |
| 10 | D5  | M1 | —  | 2/8/0     | 20/79/1 |
| 11 | D13 | M4 | —  | 3/7/0     | 35/62/3 |
| 12 | D1  | M1 | —  | 8/2/0     | 48/7/45 |
| 13 | D10 | M2 | —  | 2/8/0     | 35/64/1 |
| 14 | D15 | M3 | —  | 4/6/0     | 25/63/2 |
| 15 | D19 | M1 | —  | 3/7/0     | 21/78/1 |

(Ink Composition)

The ink composition of the present invention contains the azo iron complex dye and an oily liquid medium as an organic solvent. In the ink composition, the content of the azo iron complex dye is preferably 3-25 mass %, more preferably 5-15 mass %, and most preferably 5-10 mass %. The organic solvent may include ketone-based organic solvents, alcoholic organic solvents, and ethereal organic solvents, and among these, the ketone-based organic solvents and the alcoholic organic solvents are preferred.

The ketone-based organic solvent may include a lower alkyl ketone such as acetone, methyl ethyl ketone, dipropyl ketone, methyl isobutyl ketone, and methyl isopropyl ketone; a cyclic ketone such as cyclohexanone. Among these, methyl ethyl ketone is suitable for the ink composition for a continuous-type ink-jet printer in view of its good solubility of resins, good dispersibility of pigments, good electrical conductivity, and good ink drying properties.

The alcoholic organic solvent may include a lower alkyl alcohol such as methanol, ethanol, propanol, isopropanol, and butanol; a glycol such as dioxane, ethylene glycol, diethylene glycol, and triethylene glycol.

The ethereal organic solvent may include glycol ethers and the corresponding esters. The glycol ether may include specifically an ethylene glycol alkyl ether such as ethylene glycol monomethyl ether, ethylene glycol monoethyl ether, ethylene glycol monobutyl ether, ethylene glycol monoisopropyl ether, ethylene glycol monoisobutyl ether, ethylene glycol monophenyl glycol, ethylene glycol monobenzyl glycol, ethylene glycol dimethyl ether, and ethylene glycol diethyl ether; a diethylene glycol alkyl ether such as diethylene glycol monomethyl ether, diethylene glycol monobutyl ether, diethylene glycol monoisopropyl ether, diethylene glycol monoisobutyl ether, diethylene glycol monophenyl glycol, diethylene glycol monobenzyl glycol, diethylene glycol dimethyl ether, and diethylene glycol diethyl ether; a triethylene glycol alkyl ether such as triethylene glycol monomethyl ether, triethylene glycol monobutyl ether, triethylene glycol dimethyl ether, and triethylene glycol diethyl ether; a propylene glycol alkyl ether such as propylene glycol monomethyl ether, propylene glycol monoethyl ether, propylene glycol monopropyl ether, propylene glycol monobutyl ether, and propylene glycol monophenyl ether, a dipropylene glycol alkyl ether such as dipropylene glycol monomethyl ether, dipropylene glycol monobutyl ether, dipropylene glycol monopropyl ether, and dipropylene glycol monopropyl ether; a tripropylene glycol alkyl ether such as tripropylene glycol monomethyl ether and tripropylene glycol monobutyl ether.

In addition to the above, the organic solvent may include an ester organic solvent such as ethyl acetate, ethyl propionate, ethyl lactate, propyl acetate, and butyl acetate; an aromatic hydrocarbon organic solvent such as toluene and xylene.

The above organic solvent may be used singly or multiply.

The ink composition of the present invention may contain a resin which is soluble in the above organic solvent. Specifically, this may include a cellulose resin, a styrene-acrylic resin, a terpene phenol resin, a polyvinyl butyral resin, a ketone resin, a maleic acid resin, a rosin resin, an acrylic resin, a styrene-maleic acid resin, a polyvinyl acetal resin, a polyvinyl alcohol resin, a rosin ester resin, a silicone resin, a phenol resin, a coumarone-indene resin, a novolac resin, an aldehyde resin, a polyester resin, a polyamide resin, a polyimide resin, a terpene resin, an alkyd resin, a urethane resin, an acetal resin, an epoxy resin, a urea resin, a melamine resin, and a xylene resin. These resins may be used singly or multiply The above cellulose resin may include specifically nitrocellulose; a lower acyl-group substituted one such as cellulose propionate, cellulose butyrate, cellulose acetate, cellulose acetate propionate, and cellulose acetate butyrate; a lower alkyl-group substituted one such as methyl cellulose and ethyl cellulose; cellulose nitrate; hydroxypropyl cellulose.

There are various types of these cellulose resins depending on the degree of substitution of hydroxy groups and high and low molecular weight. The cellulose resin is appropriately selected according to the viscosity required for the ink composition. For example, this may include a cellulose ester in which the hydroxy groups of the cellulose resin are wholly or partially modified with one or more esters having 2-8 carbon atoms, preferably 2-5 carbon atoms. Specifically, the lower acyl-group substituted one such as cellulose acetate propionate and cellulose acetate butyrate is preferable. It is particularly preferable that cellulose acetate butyrate has a substitution degree of an acetyl group and a butyryl group being 2-20% and 32-53%, respectively. In addition, particularly preferred cellulose acetate propionate is that having a substitution degree of an acetyl group and a propionyl group of 0.5-10% and 35-55%, respectively. Note that the degree of substitution is defined as 100% when all three hydroxy groups of a single unit of glucose are substituted.

The styrene-acrylic resin is a copolymer of a styrene monomer with an acrylic monomer, and has preferably an acid value of 120 or less and a molecular weight of 3000-30000. The styrene monomer may include styrene, α-methylstyrene, and vinyl toluene. The acrylic monomer may include acrylic acid, methacrylic acid, methyl acrylate, methyl methacrylate, ethyl acrylate, ethyl methacrylate, propyl acrylate, propyl methacrylate, isopropyl acrylate, isopropyl methacrylate, butyl acrylate, butyl methacrylate, amyl acrylate, amyl methacrylate, hexyl acrylate, hexyl methacrylate, 2-hydroxyethyl acrylate, 2-hydroxyethyl methacrylate, 2-hydroxypropyl acrylate, and 2-hydroxypropyl methacrylate.

The styrene-acrylic resin is commercially available and may include, for example, JONCRYL (registered trademark) 68, 586 and 611 (available from BASF Co., Ltd.), Himer (registered trademark) SBM-100 and Himer SAM-955 (available from Sanyo Chemical Co., Ltd.), and Nikkalite (registered trademark) NC-6531 and Nikkalite NC-6100 (available from NIPPON CARBIDE Co., Inc.).

The terpene phenol resin is a copolymer of terpenes such as α-pinene, β-pinene and dipentene with phenols such as phenol and bisphenol. The monomers are selected according to the requirements of the ink composition, and the molar ratio of each monomer is set. The terpene phenol resin is commercially available and may include, for example, YP90 and YP90L; YS POLESTAR S145, #2100, #2115, #2130, T80, T100, TII5, T130, and T145; MightvAce G125 and G150 (all available from YASUHARA CHEMICAL Co., Ltd.).

The polyvinyl butyral resin is a copolymer of polyvinyl alcohol with butyraldehyde. According to the requirements for the ink composition, the degree of butyralization, the content of hydroxy groups and acetyl groups, and the degree of polymerization are set. The polyvinyl butyral resin has preferably a relatively low degree of polymerization from the viewpoint of the viscosity of the ink composition and the solubility in a solvent. The polyvinyl butyral resin is commercially available and may include, for example, S-LEC (registered trademark) BL-1, BL-2, BL-3, BL-S, BM-1, BM-2, BM-5, BM-S, BH-3, BH-S, BX-1, BX-2, BX-5, BX-10, BX-55 and BX-L (available from Sekisui Chemical Co., Ltd.); Denka butyral #2000-L, #3000-1, #3000-2, #3000-4, #3000-K, #4000-1, #4000-2, #5000-A and #6000-C (available from Denka Co., Ltd.).

The ketone resin is a copolymer of a ketone compound with formaldehyde, and is preferably a polymer compound having an average molecular weight of 3000 or more. The ketone resin may be chemically modified such as hydrogenated and/or end-group modified. The ketone resin is commercially available and may include, for example, HILAC (registered trademark) 111 and 222 (available from Showa Denko Materials Co., Ltd.); K-90 (available from Arakawa Chemical Co., Ltd.).

The maleic acid resin is particularly preferably a rosin-modified maleic acid resin. The rosin-modified maleic acid resin is a polyester of rosin with maleic acid and a polyvalent alcohol. The rosin-modified maleic acid resin is commercially available and may include, for example, Beckasite (registered trademark) P-720 and J-896 (available from DIC Co., Ltd.); TESPOL (registered trademark) 1101, 1103, 1104, 1105, 1150, 1151, 1152, 1155, 1158 and 1161 (available from Showa Denko Materials Co., Ltd.).

The ink composition of the present invention can be suitably used for an ink-jet printer, preferably for an industrial ink-jet printer, in particular, for a continuous-type ink-jet (CIJ) printer with charge amount control. The ink composition for a CIJ printer may contain charge control agents to obtain the desired amount of charge. In the ink composition of the present invention, a sufficient amount of charge is imparted to the ink composition due to the high electrical conductivity of the azo iron complex dye, so that usually no charge control agent is required. On the other hand, the ink composition may contain a charge control agent when a particularly high charge amount is required for the ink composition.

The charge control agent may include conductive salts, for example, salts of alkaline metals such as lithium, sodium, and potassium; salts of alkaline earth metals such as magnesium and calcium; ammonium salts and quaternary ammonium salts. The specific examples include a perchlorate, a thiocyanate, a formate, an acetate, a sulfate, a sulfonate, a propionate, a trifluoroacetate, a triflate (trifluoromethanesulfonate), a hexafluorophosphate, a hexafluoroantimonate, a tetrafluoroborate, a picrate, a carboxylate, tetrabutylammonium hexafluorophosphate, tetrabutylammonium bromide, and a tetraphenylboron quaternary ammonium salt. In addition, alkali metal halides and alkaline earth metal halides may also be included. The halides may include a fluoride, a chloride, a bromide, and an iodide. The content of the charge control agent in the ink composition is 0.1-10 mass %, preferably 0.1-5 mass %, and more preferably 0.3-3 mass %.

The ink composition humectant for a CIJ printer may contain a humectant to provide a desired droplet size when ejected from nozzles of the CIJ printer. The humectant may include surfactants, specifically anionic surfactants, cationic surfactants, nonionic surfactants, and amphoteric surfactants.

The anionic surfactants may include fatty acid salts, alkyl sulfate ester salts, alkyl aryl sulfonates, alkyl naphthalene sulfonates, dialkyl sulfonates, dialkyl sulfosuccinates, alkyl diarylether disulfonates, alkyl phosphates, polyoxyethylene alkylether sulfonates, polyoxyethylene alkyl arylether sulfonates, naphthalene sulfonate formalin condensates, polyoxyethylene alkylphosphate ester salts, glycerol borate fatty acid esters, and polyoxyethylene glycerol fatty acid esters.

The cationic surfactants may include alkylamine salts, quaternary ammonium salts, alkyl pyridinium salts, and alkyl imidazolium salts.

The nonionic surfactants may include polyoxyethylene alkyl ethers, polyoxyethylene alkyl aryl ethers, polyoxyethylene oxypropylene block copolymers, sorbitan fatty acid esters, polyoxyethylene sorbitan fatty acid esters, polyoxyethylene sorbitol fatty acid esters, glycerin fatty acid esters, polyoxyethylene fatty acid esters, polyoxyethylene alkyl amines, fluorinated nonionic surfactants, and silicone-based nonionic activators.

The amphoteric surfactants may include alkylbetaines, alkylamine oxides, and phosphatidylcholines.

The ink composition of the present invention may contain a pH adjuster to prevent precipitation of dyes, changes in ink composition due to sedimentation, and deterioration of storage stability due to discoloration. The pH adjuster is not particularly limited as long as it is added for the above purpose and can control the pH of the ink in the range of 7-8.

Specifically, the pH adjuster may include aliphatic substituted amines such as methylamine, dimethylamine, trimethylamine, ethylamine, diethylamine, triethylamine, propylamine, dipropylamine and tripropylamine; alkanolamines such as methanolamine, dimethanolamine, trimethanolamine, ethanolamine, diethanolamine, triethanolamine, propanolamine, dipropanolamine and tripropanolamine. Alkanolamines such as triethanolamine are particularly preferable from the viewpoint of suppressing discoloration.

The ink composition may contain additives in addition to or in place of charge control agents and humectants to improve print quality, ink fixability, and dissolution stability of the azo iron complex dye, and also to impart desired viscosity and surface tension. The additives may include defoamers, chemical stabilizers, UV stabilizers, and stabilizers to inhibit salt corrosion; biocides such as bactericides and fungicides.

A method for preparing the ink composition will be described. Place the azo iron complex dye, an organic solvent, a resin, and if necessary additives in a sealed container and stir. Through this step, these are mixed homogeneously and dissolved, and then filtered through a membrane filter. If necessary the mixed dissolution liquid may be heated.

The ink composition is used in a CIJ printer as follows. The ink composition stored in the ink tank flows through a flow path toward a printer head by being sucked out by a pump. The droplets of the ink composition are ejected from nozzles settled at the end of the printer head. The droplets of the ink composition are charged by passing through a charging electrode and subsequently through a deflection electrode. The droplets of the ink composition are deflected in a predetermined array so as to draw a desired character or figure, and reach the print medium passing through a tip of the deflection electrode. As a result, characters, or the like, are drawn on a print medium. For example, lot numbers and dates such as manufacturing date and expiration date are printed on the print media.

The print media, for example, are slips, cardboards, product packages, and plastic bottles. Plastics from which plastic bottles are prepared may include polyolefins such as polyethylene and polypropylene; polyvinyl chloride; polyesters such as polyamide and PET; polycarbonates; polyacetals; polyacrylates; polyurethanes, polyethers; polystyrenes; polyimides.

According to the ink composition of the present invention, by using a CIJ printer it is possible to print on glasses such as a soda-lime glass and a borosilicate glass; aforementioned plastics; metals such as aluminum, iron, tin and copper. When the print medium is a metal, good printing is possible by performing pretreatment such as roughening the metal surface by sandblasting or pickling it.

The ink composition is also suitable as an ink for writing instruments. When the ink composition is used as an ink for writing instruments, specifically as a marking pen ink, the content of the azo iron complex dye is 5-10 mass %, and when used as a ballpoint pen ink, it is 15-25 mass %.

Embodiments

The following is a more specific explanation of the present invention with reference to the examples, but the present invention is not limited to these examples. In these examples, % means mass %.

Preparation Example 1: Preparation of Disazo Dye D-1

To 592.0 g of ion-exchanged water were added 118.0 g (1.0 mol) of p-aminobenzonitrile and 339 g of 35% hydrochloric acid, and, after cooling to −3° C. in an ice bath, 178 g of 40% aqueous sodium nitrite solution was added to cause diazotization, and a diazonium salt solution was obtained.

In a separate beaker, 123.0 g (1.0 mol) of 2-amino-p-cresol and 104.0 g of 35% hydrochloric acid were added to 412 g of ion-exchanged water and dissolved. To this mixture were added 4 g of n-butanol and 140 g of ice and cooled to 2° C., and then the diazonium salt solution prepared above was added gradually. After adjusting the pH to 4.9 with 20% aqueous sodium hydroxide solution, the precipitate was filtered under reduced pressure. Washing with ion-exchanged water gave 664 g of a wet cake of the monoazo compound represented by the following chemical formula (18).

[Chemical Formula 27]

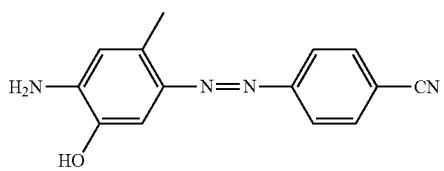

(18)

To 402 g of ion-exchanged water was added 304 g (0.42 mol) of a wet cake of the monoazo compound obtained above and dispersed under stirring. To this mixture was added gradually 49 g of 48% aqueous potassium hydroxide solution. After stirring for 30 minutes, 126 g of ion-exchanged water and 84 g of ice were added and stirred further for 30 minutes. After stirring, 75 g of 40% aqueous sodium nitrite solution was added and stirred further for 5 minutes. Then 153 g of 35% hydrochloric acid was added dropwise using a dropping funnel. After the dropwise addition, the mixture was stirred for about 1 hour to give a diazonium salt solution.

In a separate beaker, 88 g (0.40 mol) of N,N-dibutyl-aminophenol and 133 g of 48% aqueous potassium hydroxide solution were added to 1332 g of methanol and stirred under ice-cooling and dissolved. To this mixture was added dropwise the diazonium salt solution obtained above and stirred for 12 hours. The precipitate was filtered under reduced pressure and washed with ion-exchanged water to give 409 g of a wet cake. This product was dried at 80° C. to give 163.6 g of the disazo dye D-1 represented by the following chemical formula (19).

[Chemical Formula 28]

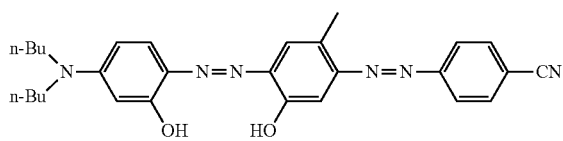

(19)

Preparation Example 2: Preparation of Disazo Dye D-2

To 200.0 g of ion-exchanged water were added 107.5 g (0.78 mol) of p-nitroaniline and 290 g of 35% hydrochloric acid and heated to 65° C. under stirring. After stirring for 1 hour, the mixture was cooled to −3° C. in an ice bath. To this mixture was added gradually 138.5 g of 40% aqueous sodium nitrite solution to cause diazotization, and a diazonium salt solution was obtained.

In a separate beaker, 96.0 g (0.78 mol) of 2-amino-p-cresol and 81.0 g of 35% hydrochloric acid were added to 500 g of ion-exchanged water and dissolved. Further, 4 g of n-butanol and 140 g of ice were added and cooled to 2° C. in an ice bath, and then to this mixture was added dropwise the diazonium salt solution obtained above. After adjusting the pH to 4.8 with 20% aqueous sodium hydroxide solution, the precipitate was filtered under reduced pressure. Washing with ion-exchanged water gave 163.1 g of a wet cake of the monoazo compound represented by the following chemical formula (20).

[Chemical Formula 29]

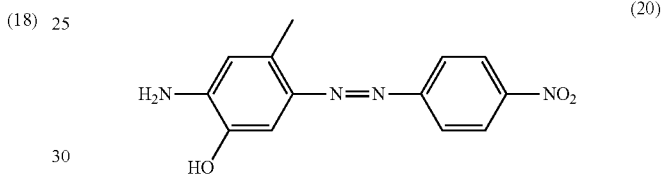

(20)

To 1643 g of N,N-dimethylformamide were added 162 g (0.60 mol) of a wet cake of the monoazo compound obtained above and 147.5 g of 35% hydrochloric acid and heated to 60° C. under stirring and dissolved. After visually confirming the absence of lumps, the mixture was cooled to 20° C. in an ice bath. To this mixture was added gradually 105.7 g of 40% aqueous sodium nitrite solution and stirred at room temperature for 2 hours to give a diazonium salt solution.

In a separate beaker, 131.7 g (0.60 mol) of N,N-dibutyl-aminophenol and 133 g of 48% aqueous potassium hydroxide solution were added to 1200 g of methanol and stirred under ice-cooling and dissolved. To this mixture was added dropwise the diazonium salt solution obtained above and stirred for 12 hours. The precipitate was filtered under reduced pressure and washed with ion-exchanged water to give 409 g of a wet cake. This product was dried at 80° C. to give 75.2 g of the disazo dye D-2 represented by the following chemical formula (21)

[Chemical Formula 30]

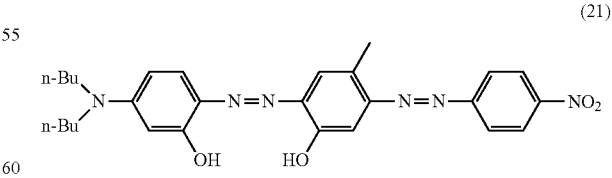

(21)

Preparation Example 3: Preparation of Disazo Dye D-3

To 600.0 g of ion-exchanged water were added 172 g (1.00 mol) of p-aminobenzenesulfonamide and 271 g of 35% hydrochloric acid and cooled to −3° C. in an ice bath. To this mixture was added gradually 179.3 g of 40% aqueous sodium nitrite solution. Further, 2.4 g of urea was added to cause diazotization, and a diazonium salt solution was obtained.

In a separate beaker, 123.4 g (1.00 mol) of 2-amino-p-cresol and 125.0 g of 35% hydrochloric acid were added to 440 g of ion-exchanged water and dissolved. Then 4 g of n-butanol and 140 g of ice were added and cooled to 2° C. in an ice bath, and to this mixture was added dropwise the diazonium salt solution obtained above. After adjusting the pH to 4.8 with 20% aqueous sodium hydroxide solution, the precipitate was filtered under reduced pressure. Washing with ion-exchanged water gave 719.5 g of a wet cake of the monoazo compound represented by the following chemical formula (22).

[Chemical Formula 31]

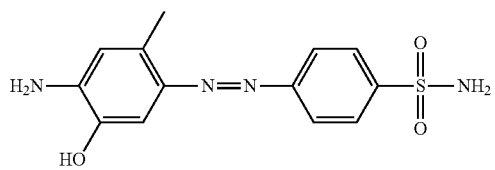

(22)

To 700 g of ion-exchanged water was dispersed 700 g (0.90 mol) of a wet cake of the monoazo compound obtained above, and then 82.7 g of 48% aqueous sodium hydroxide solution was added gradually and stirred for 1 hour. To this mixture was added 700 g of ice in an ice bath and cooled to 1° C., and then 162.0 g of 40% aqueous sodium nitrite solution was added gradually. After stirring for a while, 300 g of ice was added, and to this mixture was added gradually 287.0 g of 35% hydrochloric acid and stirred at room temperature for 2 hours to give a diazonium salt solution.

In a separate beaker, 193.2 g (0.88 mol) of N,N-dibutyl-aminophenol and 217.5 g of 48% aqueous sodium hydroxide solution were added to 690 g of methanol and stirred under ice-cooling and dissolved. To this mixture was added dropwise the diazonium salt solution obtained above and stirred for 12 hours. After adjusting the pH to 4.0 with 35% hydrochloric acid, the mixture was heated to 35° C. and stirred for 1 hour. The precipitate was filtered under reduced pressure and washed with ion-exchanged water to give 441.1 g of a wet cake. This product was dried at 80° C. to give 175.2 g of the disazo dye D-3 represented by the following chemical formula (23).

[Chemical Formula 32]

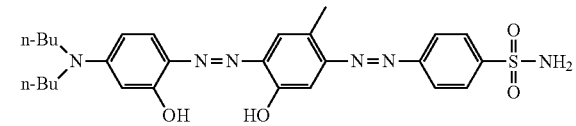

(23)

Preparation Example 4. Preparation of Disazo Dye D-4

To 688.0 g of ion-exchanged water were added 67.6 g (0.50 mol) of 4-acetaminophenone and 114.6 g of 35% hydrochloric acid and cooled to −3° C. in an ice bath. To this mixture was added gradually 90.6 g of 40% aqueous sodium nitrite solution to cause diazotization. After stirring for 1 hour, 1.9 g of thiourea was added to give a diazonium salt solution.

In a separate beaker, 61.6 g (0.50 mol) of 2-amino-p-cresol and 52.1 g of 35% hydrochloric acid were added to 1111 g of methanol and dissolved. After cooling to 5° C. in an ice bath, to this mixture was added dropwise the diazonium salt solution obtained above. The precipitate was filtered under reduced pressure followed by washing with ion-exchanged water, and dried at 80° C. to give 56.3 g of the monoazo compound represented by the following chemical formula (24).

[Chemical Formula 33]

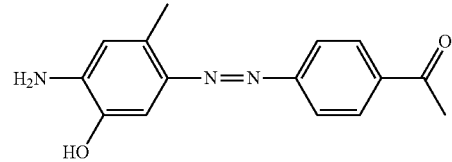

(24)

To 415 g of N,N-dimethylformamide solution were added 56.0 g (0.18 mol) of the monoazo compound obtained above and 45.4 g of 35% hydrochloric acid and cooled to 2° C. by addition of 84 g of ice in an ice bath. To this mixture was added gradually 32.6 g of 40% aqueous sodium nitrite solution and stirred for 1 hour followed by addition of 1.8 g of sulfamic acid to give a diazonium salt solution.

In a separate beaker, 40.6 g (0.18 mol) of N,N-dibutyl-aminophenol and 79.1 g of 20% aqueous sodium hydroxide solution were added to 612.1 g of methanol and stirred under ice-cooling and dissolved. To this mixture was added dropwise the diazonium salt solution obtained above and stirred for 3 hours. The precipitate was filtered under reduced pressure and washed with methanol followed by drying at 80° C. to give 15.9 g of the disazo dye D-4 represented by the following chemical formula (25).

[Chemical Formula 34]

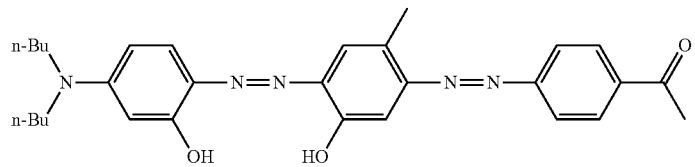

(25)

Preparation Example 5: Preparation of Monoazo Dye M-1

To 50.0 g of isopropanol were added 7.5 g (0.05 mol) of 5-nitro-2-aminophenol and 13.6 g of 35% hydrochloric acid and dissolved followed by diazotization by gradual addition of 8.0 g of 40% aqueous sodium nitrite solution in an ice bath to give a diazonium salt solution.

In a separate beaker, to 200 g of water were added 26.1 g of 20% aqueous sodium hydroxide solution and further 6.6 g of 2-naphthol and dispersed. To this dispersion liquid was added dropwise the diazonium salt solution obtained above and reacted for 3 hours. Then, after adjusting the pH to 2.8, the precipitated monoazo compound was filtered and washed with water to give 82.5 g of a wet cake of the monoazo dye M-1 represented by the following chemical formula (26).

[Chemical Formula 35]

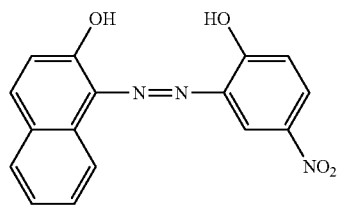

(26)

Preparation Example 6: Preparation of Monoazo Dye M-2

To 50.0 g of isopropanol were added 7.5 g (0.05 mol) of 4-nitro-2-aminophenol and 13.6 g of 35% hydrochloric acid and dissolved followed by diazotization by gradual addition of 8.0 g of 40% aqueous sodium nitrite solution in an ice bath to give a diazonium salt solution.

In a separate beaker, to 200 g of water were added 26.1 g of 20% aqueous sodium hydroxide solution and further 6.6 g (0.05 mol) of 2-naphthol and dispersed. To this dispersion liquid was added dropwise the diazonium salt solution obtained above and reacted for 3 hours. Then, after adjusting the pH to 2.8, the precipitated monoazo compound was filtered and washed with water to give 81.8 g of a wet cake of the monoazo dye M-2 represented by the following chemical formula (27).

[Chemical Formula 36]

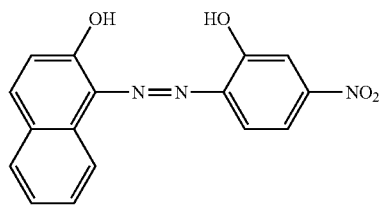

(27)

Preparation Example 7. Preparation of Monoazo Dye M-3

To 50.0 g of isopropanol were added 7.0 g (0.05 mol) of 4-chloro-2-aminophenol and 13.6 g of 35% hydrochloric acid and dissolved followed by diazotization by gradual addition of 8.0 g of 40% aqueous sodium nitrite solution in an ice bath to give a diazonium salt solution.

In a separate beaker, to 200 g of water were added 26.1 g of 20% aqueous sodium hydroxide solution and further 6.6 g (0.05 mol) of 2-naphthol and dispersed. To this dispersion liquid was added dropwise the diazonium salt solution obtained above and reacted for 3 hours. Then, after adjusting the pH to 2.8, the precipitated monoazo compound was filtered and washed with water to give 80.1 g of a wet cake of the monoazo dye M-3 represented by the following chemical formula (28).

[Chemical Formula 37]

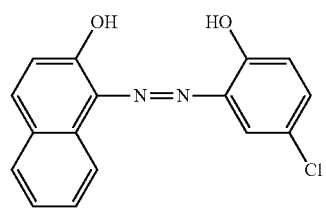

(28)

Preparation Example 8: Preparation of Monoazo Dye M-4

To 50.0 g of isopropanol were added 7.0 g (0.05 mol) of 4-chloro-2-aminophenol and 13.6 g of 35% hydrochloric acid and dissolved followed by diazotization by gradual addition of 8.0 g of 40% aqueous sodium nitrite solution in an ice bath to give a diazonium salt solution.

In a separate beaker, to 200 g of water were added 26.1 g of 20% aqueous sodium hydroxide solution and further 6.6 g (0.05 mol) of 2-naphthol and dispersed. To this dispersion liquid was added dropwise the diazonium salt solution obtained above and reacted for 3 hours. Then, after adjusting the pH to 2.8, the precipitated monoazo compound was filtered and washed with water to give 80.1 g of a wet cake of the monoazo dye M-4 represented by the following chemical formula (29).

[Chemical Formula 38]

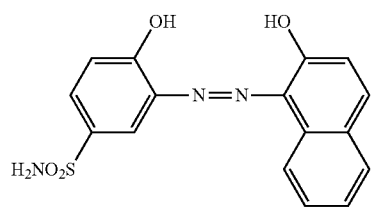

(29)

Preparation Example 9: Preparation of Monoazo Dye M-5

To 182.0 g of isopropanol were added 34.0 g (0.24 mol) of 4-chloro-2-aminophenol and 82.2 g of 35% hydrochloric acid and dissolved followed by diazotization by gradual addition of 48.9 g of 40% aqueous sodium nitrite solution in an ice bath to give a diazonium salt solution.

In a separate beaker, to 182 g of isopropanol were added 107.2 g of 20% aqueous sodium hydroxide solution and further 60.7 g (0.24 mol) of 6-tert-octyl-2-naphthol and dissolved. To this solution was added dropwise the diazonium salt solution obtained above and reacted for 2 hours. Then the precipitate was filtered, washed with water, and dried to give 93.5 g of the monoazo dye M-5 represented by the following chemical formula (30).

[Chemical Formula 39]

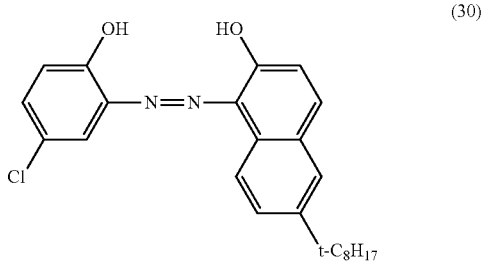

(30)

[Chemical Formula 40]

Example 1: Preparation of Azo Iron Complex Dye A-1

To 120 g of N,N-dimethylformamide solution were added 5.3 g (0.011 mol) of the disazo dye D-1 obtained in Preparation example 1 and 22.1 g (moisture content 40%, 0.043 mol) of the monoazo dye M-1 as a wet cake obtained in Preparation example 5, and the mixture was stirred at 55° C. for 1 hour (disazo dye:monoazo dye=2:8 mol). To this mixture was added dropwise 12.4 g (0.013 mol) of 41% aqueous ferric sulfate solution, and, after completion of the dropwise addition, the mixture was heated to 120° C. and stirred for 3 hours. After completion of the reaction, the mixture was cooled to room temperature, and then the pH was adjusted to 10.0 with 9.0 g of 20% aqueous sodium hydroxide solution. To this solution was added gradually 103.6 g of 5% aqueous solution of tert-alkyl ($C_{12}$-$C_{14}$) primary amine (available from Dow Chemical Co. Ltd.; trade name PRIMENE 81-R), and the mixture was stirred at 40° C. for 1 hour. Then the precipitate was filtered, washed with water, and dried to give 23.1 g of the azo iron complex dye A-1 which contains the disazo-monoazo iron complex (DM-form) represented by the following chemical formula (31DM), the monoazo-monoazo iron complex (MM-form) represented by the following chemical formula (31MM), and the disazo-disazo iron complex (DD-form) represented by the following chemical formula (31DD).

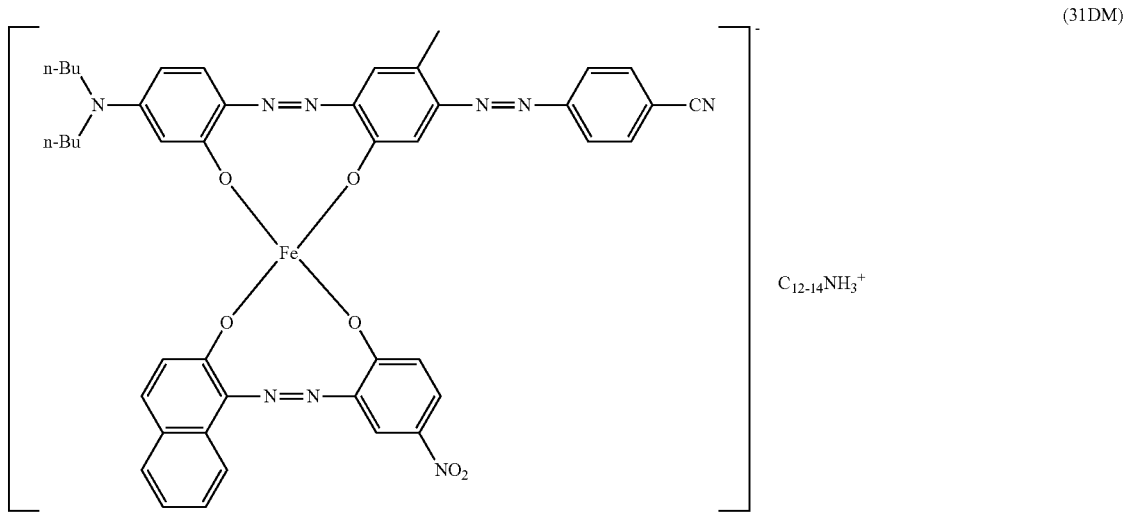

(31DM)

[Chemical Formula 41]

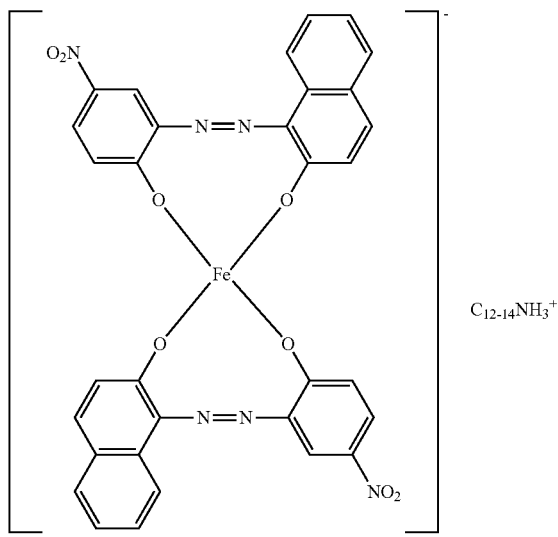

(31MM)

[Chemical Formula 42]

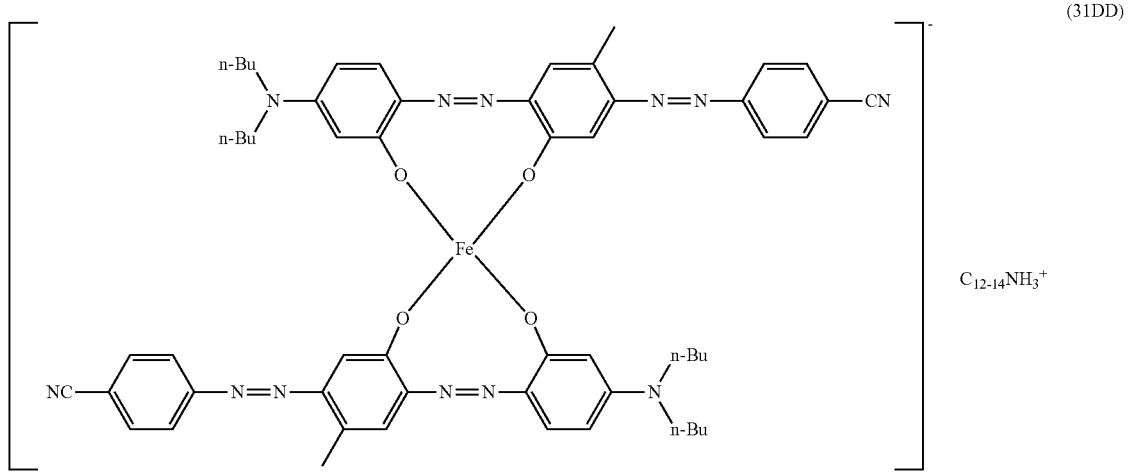

(31DD)

(Absorbance Measurement)

A solution of the azo iron complex dye A-1 in methyl ethyl ketone was prepared at a concentration of 10 mg/1000 ml (10 ppm). The absorbance of this solution was measured using an ultraviolet-visible spectrophotometer (available from Shimadzu Corporation; trade name UV-1700). The visible absorption spectrum of the azo iron complex dye A-1 is shown in FIG. 1. A solution with the azo iron complex dye A-1 adjusted to a concentration of 5% exhibited a sufficient black color.

(Electrical Conductivity Measurement)

A 6% solution of the azo iron complex dye A-1 in methyl ethyl ketone was prepared and measured using an electrical conductivity meter (available from Eutech Instruments Pte, Ltd.; trade name CyberScan CON100). As a result, the electrical conductivity K was 1530 μS/cm. Furthermore, a 6% solution of the azo iron complex dye A-1 in methyl ethyl ketone was prepared and measured using a conductivity meter (available from Knick Co., Ltd.; trade name Conducell 4USF-PG120). As a result, the electrical conductivity K was 1530 sS/cm.

(Measurement of Alkaline Metal Ion Content)

The content of an alkaline metal ion (Na ion) in the azo iron complex dye was measured using an atomic absorption spectrophotometer (available from Varian Technologies Japan Ltd.; trade name SpectrAA-220FS). As a result, the content of the alkaline metal ion was 1000 ppm or less.

Example 2: Preparation of Azo Iron Complex Dye A-2

To 100 g of N,N-dimethylformamide solution were added 9.69 g (0.020 mol) of the disazo dye D-1 obtained in Preparation example 1 and 10.6 g (moisture content 42%, 0.020 mol) of the monoazo dye M-2 as a wet cake obtained in Preparation example 6, and the mixture was stirred at 55° C. for 1 hour (disazo dye:monoazo dye=5:5 mol). To this mixture was added dropwise 9.5 g (0.010 mol) of 41% aqueous ferric sulfate solution, and, after completion of the dropwise addition, the mixture was heated to 120° C. and stirred for 3 hours. After completion of the reaction, the mixture was cooled to room temperature, and then the pH was adjusted to 10.1 with 9.0 g of 20% aqueous sodium hydroxide solution. To this solution was added gradually 80.6 g of 5% aqueous solution of tert-alkyl ($C_{12}$-$C_{14}$) primary amine (available from Dow Chemical Co. Ltd., trade name PRIMENE 81-R), and the mixture was stirred at 40° C. for 1 hour. Then the precipitate was filtered, washed with water, and dried to give 15.6 g of the azo iron complex dye A-2 which contains the DM-form represented by the following chemical formula (32DM), the MM-form represented by the following chemical formula (32MM), and the DD-form represented by the following chemical formula (32DD).

[Chemical Formula 43]

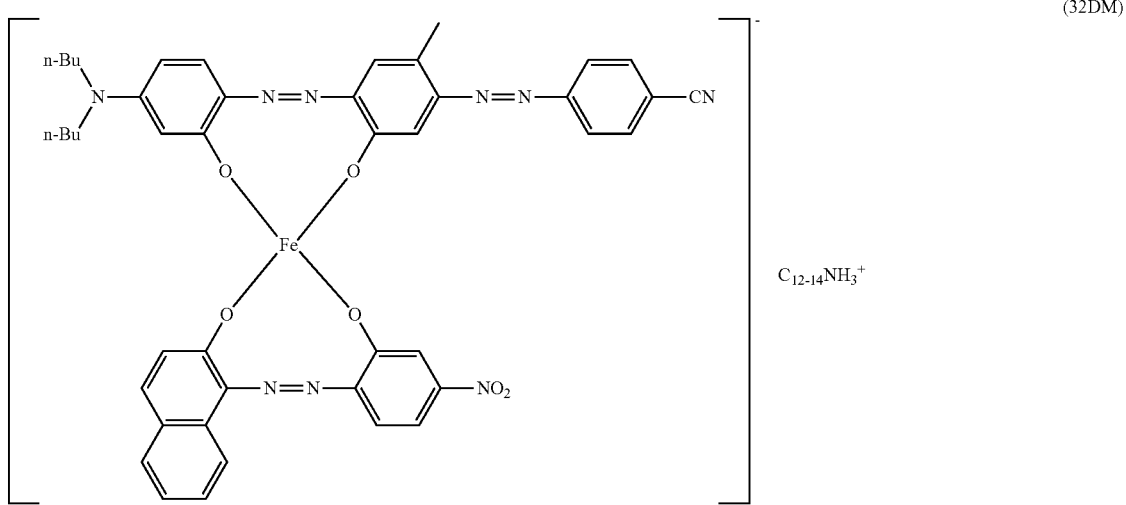

(32DM)

[Chemical Formula 44]

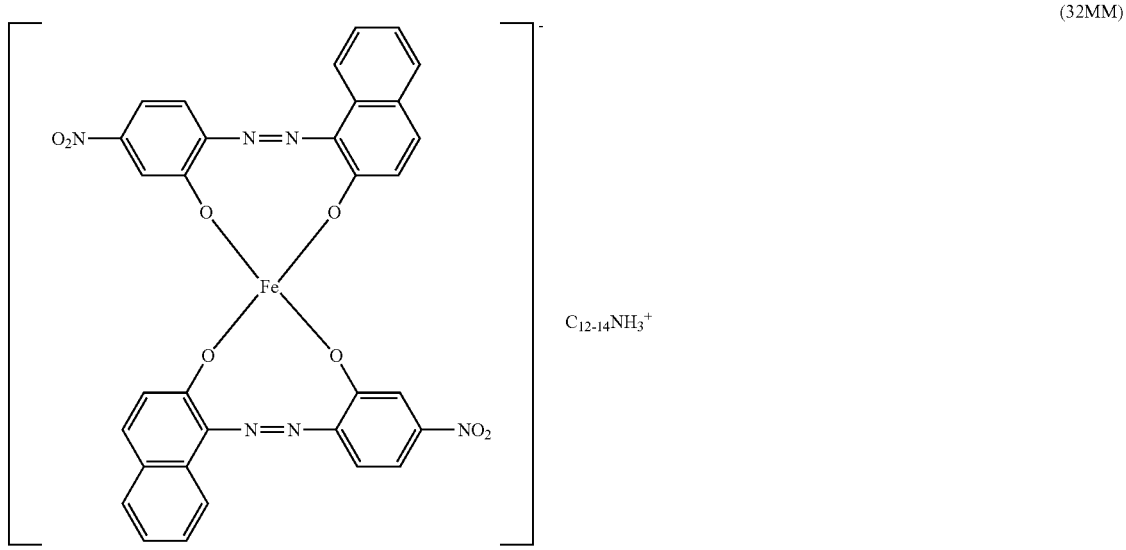

(32MM)

[Chemical Formula 45]

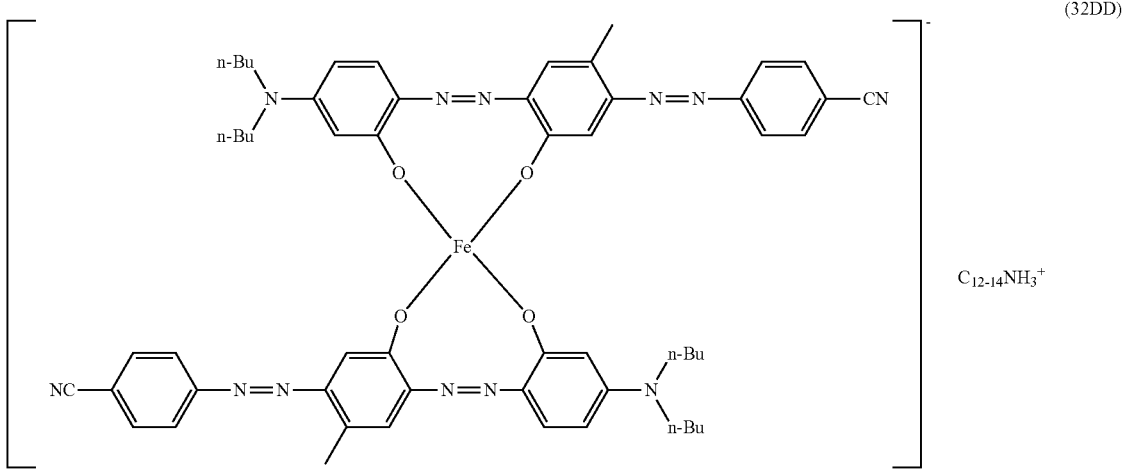

(32DD)

Figure 2:
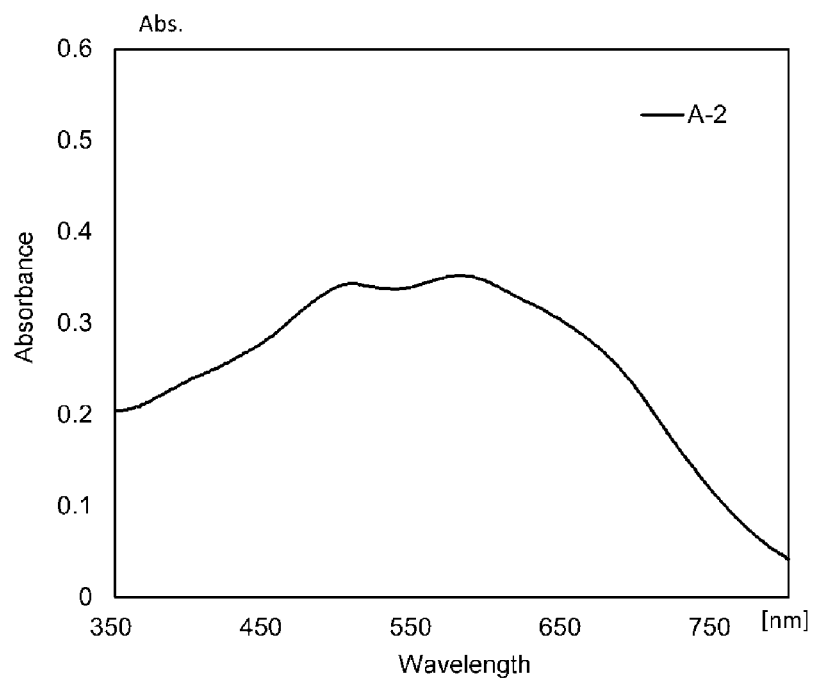
FIG. 2 shows a visible absorption spectrum of the azo iron complex dye A-2 in Example 2 applying the present invention.

The absorbance, the electrical conductivity, and the content of an alkaline metal ion of the azo iron complex dye A-2 were measured in the same manner as the azo iron complex dye A-1. The visible absorption spectrum of the azo iron complex dye A-2 is shown in FIG. 2. A solution with the azo iron complex dye A-2 adjusted to a concentration of 5% exhibited a sufficient black color. And the electrical conductivity K of the azo iron complex dye A-2 was 908 μS/cm and the content of the alkaline metal ion was 1000 ppm or less.

Example 3: Preparation of Azo Iron Complex Dye A-3

To 100 g of N,N-dimethylformamide solution were added 5.33 g (0.011 mol) of the disazo dye D-1 obtained in Preparation example 1 and 21.9 g (moisture content 40%, 0.044 mol) of the monoazo dye M-3 as a wet cake obtained in Preparation example 7, and the mixture was stirred at 55° C. for 1 hour (disazo dye:monoazo dye=2:8 mol). To this mixture was added dropwise 12.9 g (0.013 mol) of 41% aqueous ferric sulfate solution, and, after completion of the dropwise addition, the mixture was heated to 120° C. and stirred for 3 hours. After completion of the reaction, the mixture was cooled to room temperature, and then the pH was adjusted to 10.2 with 9.0 g of 20% aqueous sodium hydroxide solution. To this solution was added gradually 103.0 g of 5% aqueous solution of tert-alkyl ($C_{12}$-$C_{14}$) primary amine (available from Dow Chemical Co. Ltd.; trade name PRIMENE 81-R), and the mixture was stirred at 40° C. for 1 hour. Then the precipitate was filtered, washed with water, and dried to give 17.8 g of the azo iron complex dye A-3 which contains the DM-form represented by the following chemical formula (33DM), the MM-form represented by the following chemical formula (33MM), and the DD-form represented by the following chemical formula (33DD).

[Chemical Formula 46]

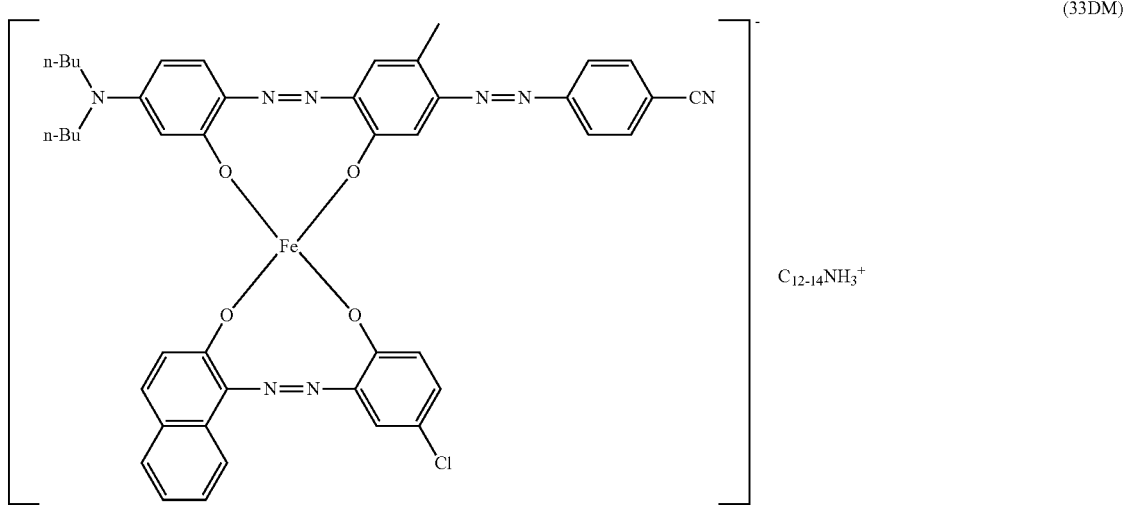

(33DM)

[Chemical Formula 47]

(33MM)

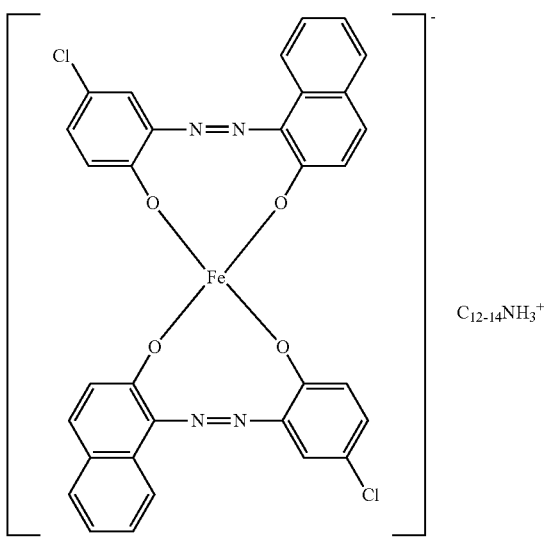

[Chemical Formula 48]

(33DD)

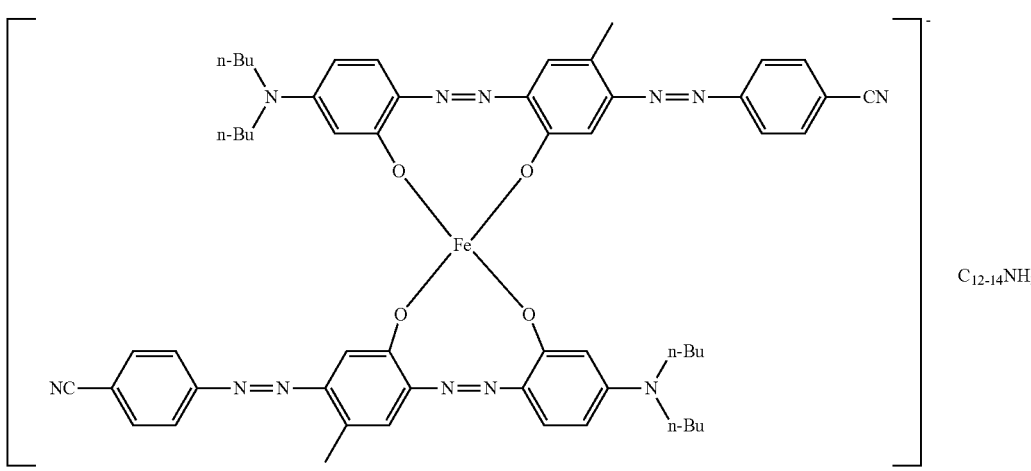

The absorbance, the electrical conductivity, and the content of an alkaline metal ion of the azo iron complex dye A-3 were measured in the same manner as the azo iron complex dye A-1. The visible absorption spectrum of the azo iron complex dye A-3 is shown in FIG. 3. A solution with the azo iron complex dye A-3 adjusted to a concentration of 5% exhibited a sufficient black color. And the electrical conductivity K of the azo iron complex dye A-3 was 1260 μS/cm and the content of the alkaline metal ion was 1000 ppm or less.

Example 4: Preparation of Azo Iron Complex Dye A-4

To 100 g of N,N-dimethylformamide solution were added 5.55 g (0.011 mol) of the disazo dye D-2 obtained in Preparation example 2 and 21.9 g (moisture content 40%, 0.043 mol) of the monoazo dye M-2 as a wet cake obtained in Preparation example 6, and the mixture was stirred at 55° C. for 1 hour (disazo dye:monoazo dye=2:8 mol). To this mixture was added dropwise 12.4 g (0.013 mol) of 41% aqueous ferric sulfate solution, and, after completion of the dropwise addition, the mixture was heated to 120° C. and stirred for 3 hours. After completion of the reaction, the mixture was cooled to room temperature, and then the pH was adjusted to 10.1 with 9.0 g of 20% aqueous sodium hydroxide solution. To this solution was added gradually 102.8 g of 5% aqueous solution of tert-alkyl ($C_{12}$-$C_{14}$) primary amine (available from Dow Chemical Co. Ltd.; trade name PRIMENE 81-R), and the mixture was stirred at 40° C. for 1 hour. Then the precipitate was filtered, washed with water, and dried to give 16.5 g of the azo iron complex dye A-4 which contains the DM-form represented by the following chemical formula (34DM), the MM-form represented by the following chemical formula (34MM), and the DD-form represented by the following chemical formula (34DD).

[Chemical Formula 49]
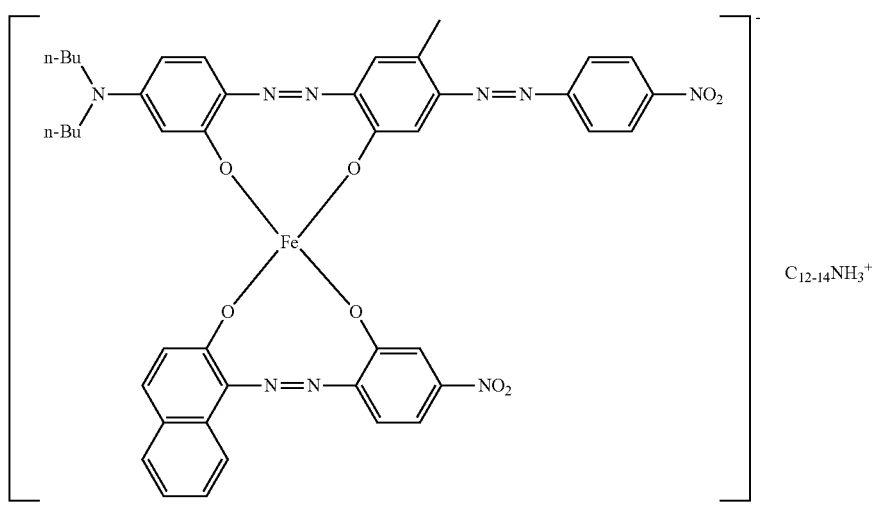
(34DM)
[Chemical Formula 50]
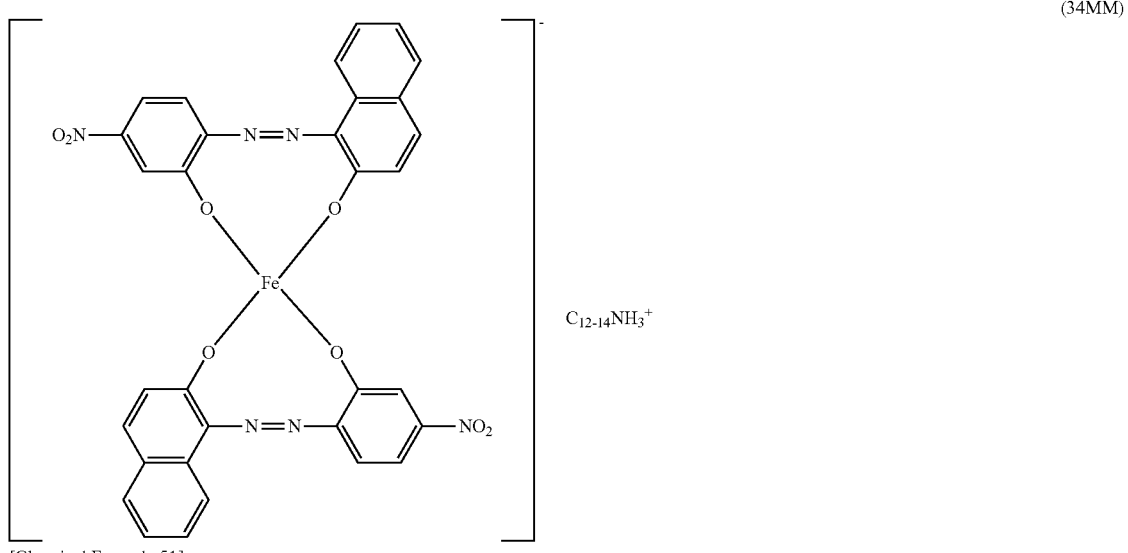
(34MM)
[Chemical Formula 51]
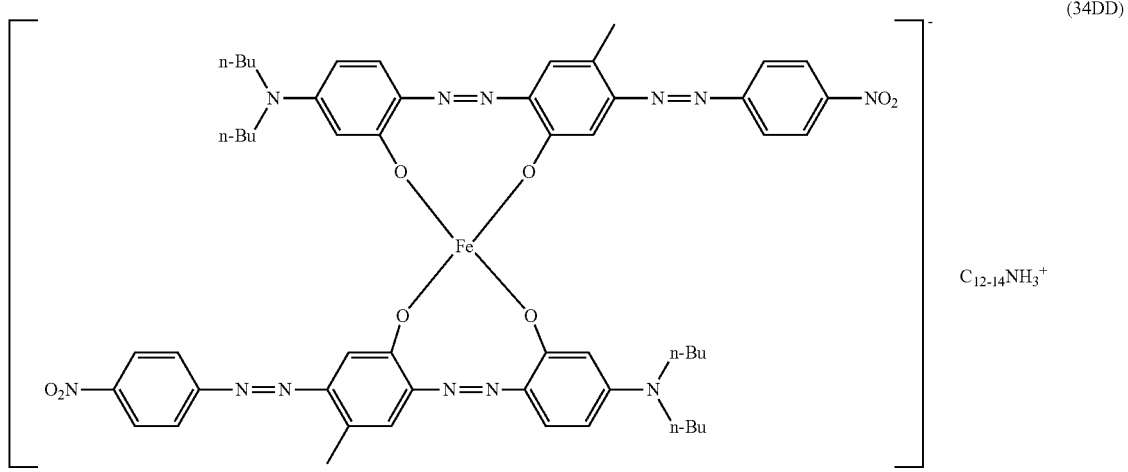
(34DD)

The absorbance, the electrical conductivity, and the content of an alkaline metal ion of the azo iron complex dye A-4 were measured in the same manner as the azo iron complex dye A-1. The visible absorption spectrum of the azo iron complex dye A-4 is shown in FIG. 4. A solution with the azo iron complex dye A-4 adjusted to a concentration of 5% exhibited a sufficient black color. And the electrical conductivity K of the azo iron complex dye A-4 was 1275 μS/cm and the content of the alkaline metal ion was 1000 ppm or less.

Example 5: Preparation of Azo Iron Complex Dye A-5

To 120 g of N,N-dimethylformamide solution were added 12.9 g (0.024 mol) of the disazo dye D-3 obtained in Preparation example 3 and 18.7 g (moisture content 40%, 0.036 mol) of the monoazo dye M-2 as a wet cake obtained in Preparation example 6, and the mixture was stirred at 55° C. for 1 hour (disazo dye:monoazo dye=4:6 mol). To this mixture was added dropwise 15.0 g (0.015 mol) of 41% aqueous ferric sulfate solution, and, after completion of the dropwise addition, the mixture was heated to 120° C. and stirred for 3 hours. After completion of the reaction, the mixture was cooled to room temperature, and then the pH was adjusted to 9.9 with 9.0 g of 20% aqueous sodium hydroxide solution. To this solution was added gradually 125.3 g of 5% aqueous solution of tert-alkyl ($C_{12}$-$C_{14}$) primary amine (available from Dow Chemical Co. Ltd.; trade name PRIMENE 81-R), and the mixture was stirred at 40° C. for 1 hour. Then the precipitate was filtered, washed with water, and dried to give 15.9 g of the azo iron complex dye A-5 which contains the DM-form represented by the following chemical formula (35DM), the MM-form represented by the following chemical formula (35MM), and the DD-form represented by the following chemical formula (35DD).

[Chemical formula 52]

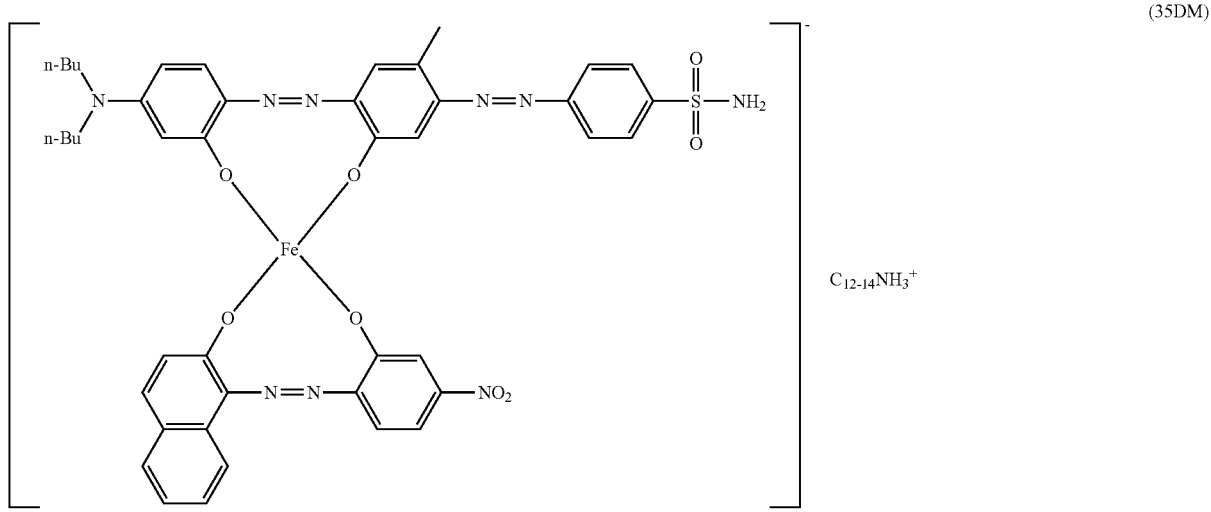

(35DM)

[Chemical formula 53]

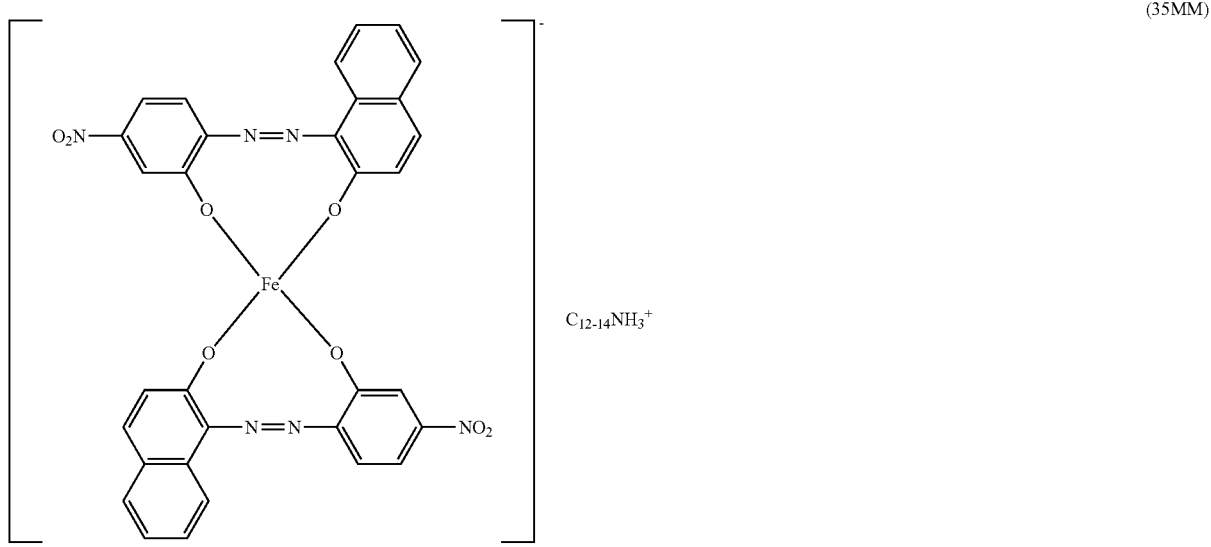

(35MM)

[Chemical formula 54]

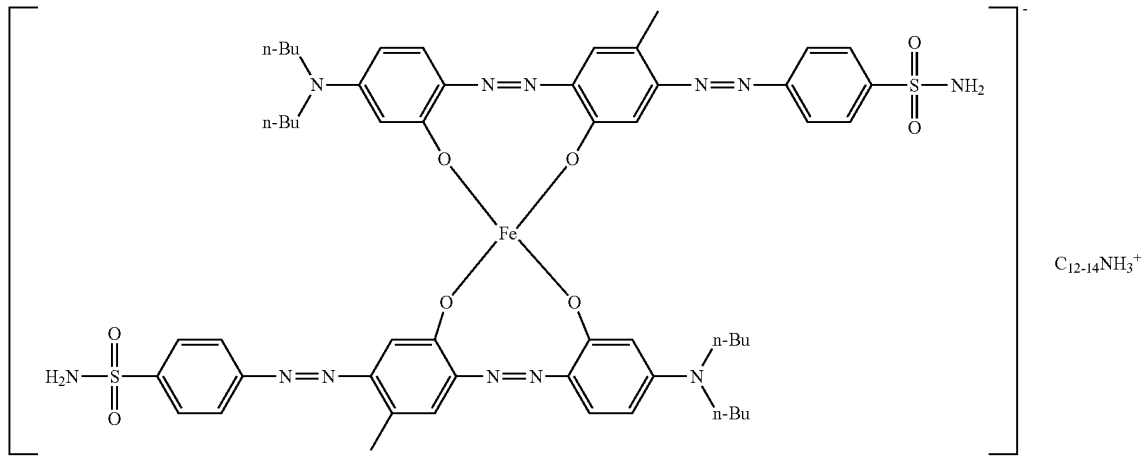

(35DD)

The absorbance, the electrical conductivity, and the content of an alkaline metal ion of the azo iron complex dye A-5 were measured in the same manner as the azo iron complex dye A-1. The visible absorption spectrum of the azo iron complex dye A-5 is shown in FIG. 5. A solution with the azo iron complex dye A-5 adjusted to a concentration of 5% exhibited a sufficient black color. And the electrical conductivity K of the azo iron complex dye A-5 was 920 μS/cm and the content of the alkaline metal ion was 1000 ppm or less.

Example 6: Preparation of Azo Iron Complex Dye A-6

To 120 g of N,N-dimethylformamide solution were added 5.3 g (0.011 mol) of the disazo dye D-1 obtained in Preparation example 1, 11.2 g (moisture content 40%, 0.022 mol) of the monoazo dye M-1 as a wet cake obtained in Preparation example 5, and 11.6 g (moisture content 42%, 0.022 mol) of the monoazo dye M-2 as a wet cake obtained in Preparation example 6, and the mixture was stirred at 55° C. for 1 hour (disazo dye:monoazo dye 1:monoazo dye 2=2:4:4 mol). To this mixture was added dropwise 12.4 g (0.013 mol) of 41% aqueous ferric sulfate solution, and, after completion of the dropwise addition, the mixture was heated to 120° C. and stirred for 3 hours. After completion of the reaction, the mixture was cooled to room temperature, and then the pH was adjusted to 10.1 with 9.0 g of 20% aqueous sodium hydroxide solution. To this solution was added gradually 100.4 g of 5% aqueous solution of tert-alkyl ($C_{12}$-$C_{14}$) primary amine (available from Dow Chemical Co. Ltd.; trade name PRIMENE 81-R), and the mixture was stirred at 40° C. for 1 hour. Then the precipitate was filtered, washed with water, and dried to give 14.4 g of the azo iron complex dye A-6 which contains the DM-form represented by the following chemical formula (36DM), the MM-form represented by the following chemical formula (36MM), and the DD-form represented by the following chemical formula (36DD).

[Chemical formula 55]

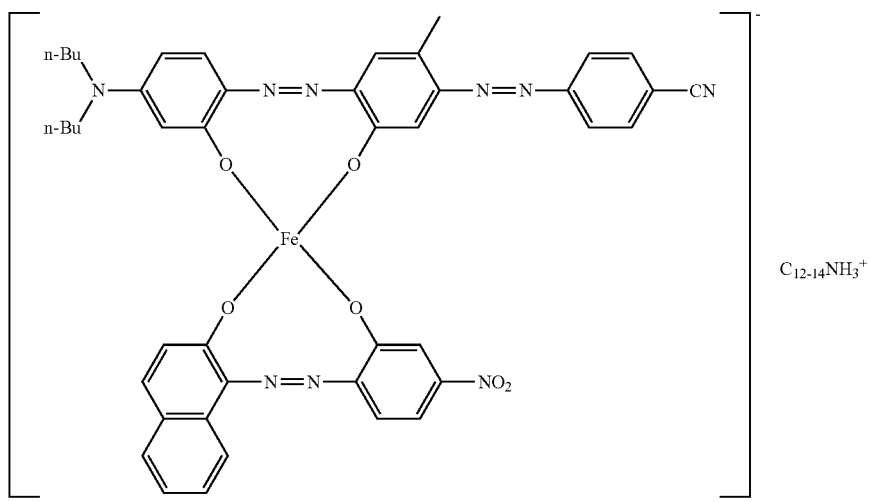

(36DM)

-continued
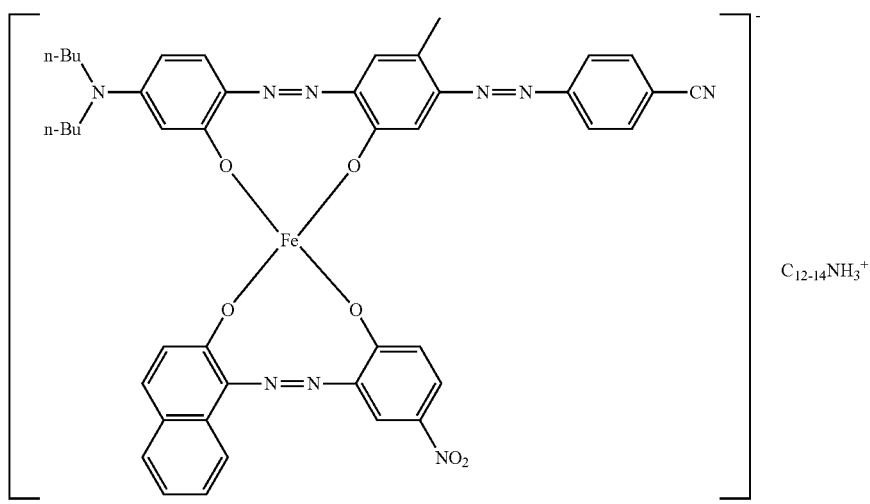
[Chemical formula 56]
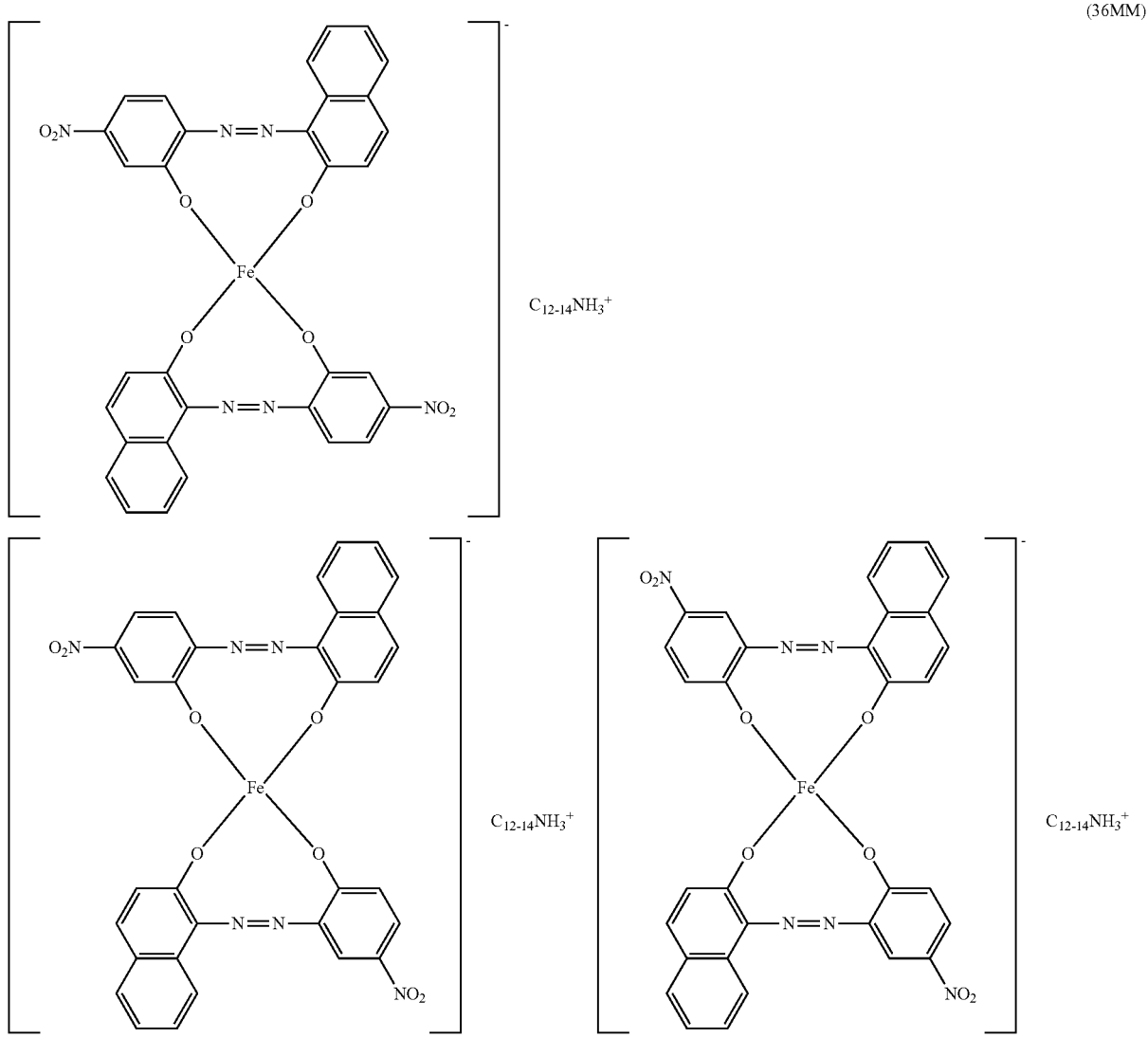
(36MM)

[Chemical formula 57]

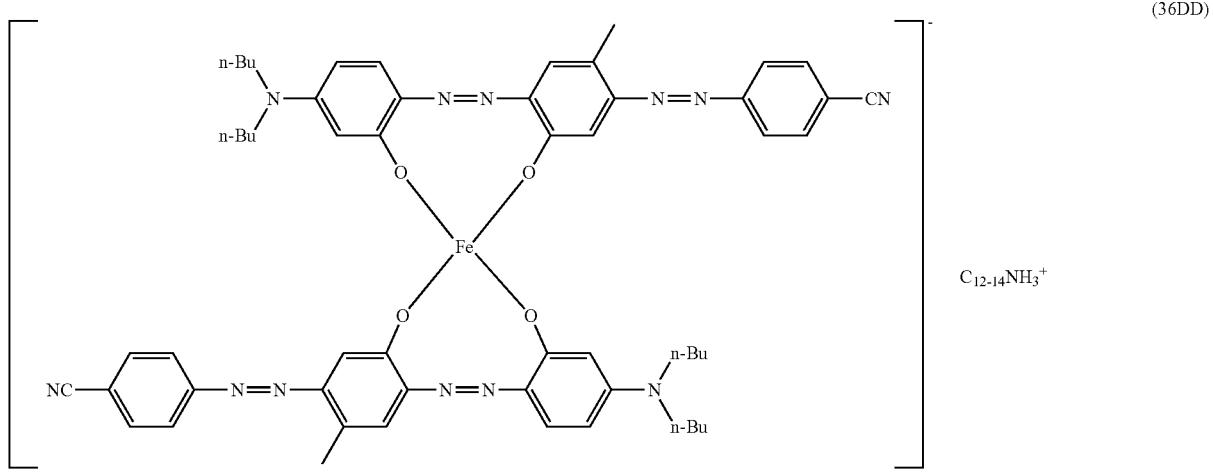

(36DD)

The absorbance, the electrical conductivity, and the content of an alkaline metal ion of the azo iron complex dye A-6 were measured in the same manner as the azo iron complex dye A-1. The visible absorption spectrum of the azo iron complex dye A-6 is shown in FIG. 6. As can be seen from this figure, a solution with the azo iron complex dye A-6 adjusted to a concentration of 5% exhibited a sufficient black color. And the electrical conductivity K of the azo iron complex dye A-6 was 1450 μS/cm and the content of the alkaline metal ion was 1000 ppm or less.

Example 7: Preparation of Azo Iron Complex Dye A-7

To a mixture of 200 g of ion-exchanged water, 12 g of n-butanol, and 48 g of 20% aqueous sodium hydroxide solution were added 12.9 g (0.024 mol) of the disazo dye D-3 obtained in Preparation example 5 and 32.0 g (moisture content 40%, 0.056 mol) of the monoazo dye M-4 as a wet cake obtained in Preparation example 8, and the mixture was stirred at 70° C. for 30 minutes (disazo dye:monoazo dye=3:7 mol). To this mixture was added dropwise 20.0 g (0.021 mol) of 41% aqueous ferric sulfate solution, and, after completion of the dropwise addition, the mixture was heated to 90° C. and stirred for 3 hours. After completion of the reaction, the mixture was cooled to room temperature, and then to this solution was added gradually 191.3 g of 5% aqueous solution of tert-alkyl ($C_{12}$-$C_{14}$) primary amine (available from Dow Chemical Co. Ltd.; trade name PRIMENE 81-R), and the mixture was stirred at 40° C. for 1 hour. Then the precipitate was filtered, washed with water, and dried to give 40.2 g of the azo iron complex dye A-7 which contains the DM-form represented by the following chemical formula (37DM), the MM-form represented by the following chemical formula (37MM), and the DD-form represented by the following chemical formula (37DD).

[Chemical formula 58]

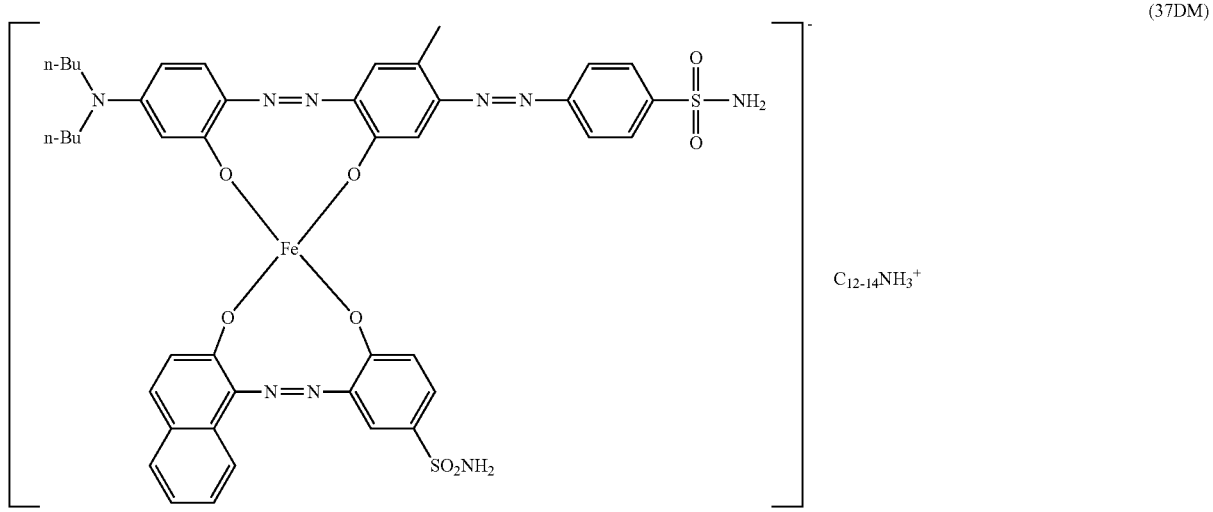

(37DM)

[Chemical formula 59]

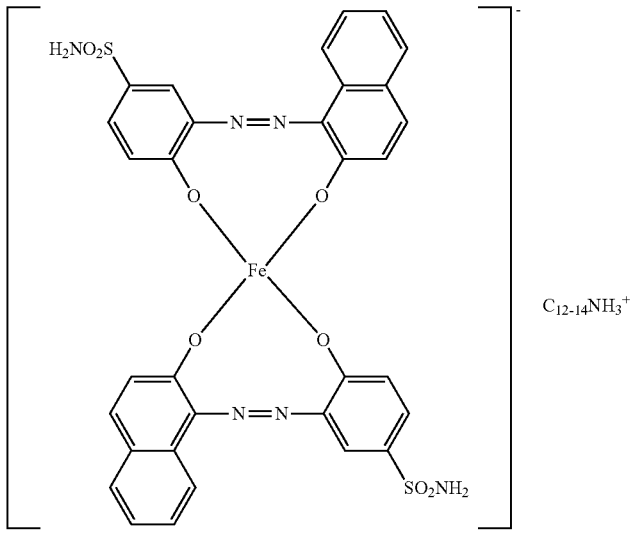

(37MM)

[Chemical formula 60]

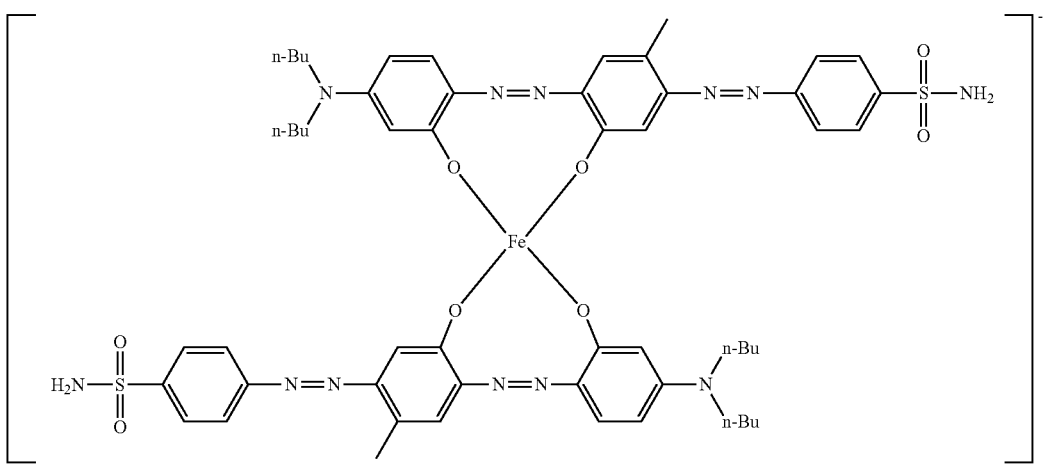

(37DD)

The absorbance, the electrical conductivity, and the content of an alkaline metal ion of the azo iron complex dye A-7 were measured in the same manner as the azo iron complex dye A-1. The visible absorption spectrum of the azo iron complex dye A-7 is shown in FIG. 7. A solution with the azo iron complex dye A-7 adjusted to a concentration of 5% exhibited a sufficient black color. And the electrical conductivity K of the azo iron complex dye A-7 was 826 μS/cm and the content of the alkaline metal ion was 1000 ppm or less.

Comparative Example 1: Preparation of Azo Iron Complex Dye B-1

To 12.5 g of 20% aqueous sodium hydroxide solution were added 42.5 g (moisture content 42%, 0.080 mol) of the monoazo dye M-2 as a wet cake obtained in Preparation example 6, 120 g of ion-exchanged water, and 5.7 g of n-butanol, and the mixture was stirred at 90° C. for 1 hour (disazo dye:monoazo dye=0:10 mol). To this mixture was added dropwise 40.7 g (0.042 mol) of 41% aqueous ferric sulfate solution, and, after completion of the dropwise addition, the mixture was heated to 90° C. and stirred for 3 hours. After completion of the reaction, the mixture was allowed to cool to room temperature, and then the pH was adjusted to 10.1 with 9.0 g of 20% aqueous sodium hydroxide solution. To this solution was added gradually 100.4 g of 5% aqueous solution of tert-alkyl ($C_{12}$-$C_{14}$) primary amine (available from Dow Chemical Co. Ltd., trade name PRIMENE 81-R), and the mixture was stirred at 40° C. for 1 hour. Then the precipitate was filtered, washed with water, and dried. As a result, as represented by the following chemical formula (38MM), 27.4 g of the azo iron complex dye B-1 consisting of only the monoazo-monoazo iron complex was obtained.

[Chemical formula 61]

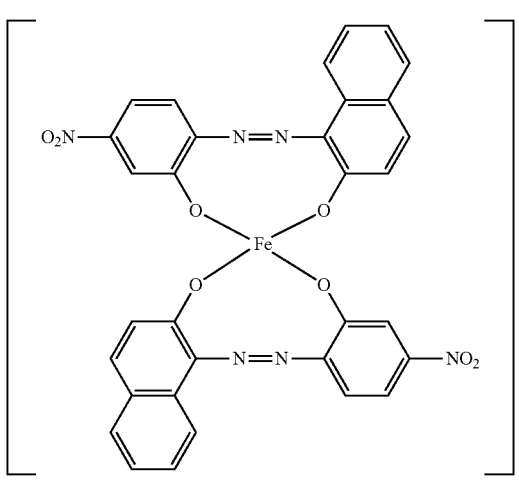

(38MM)

[Chemical formula 62]

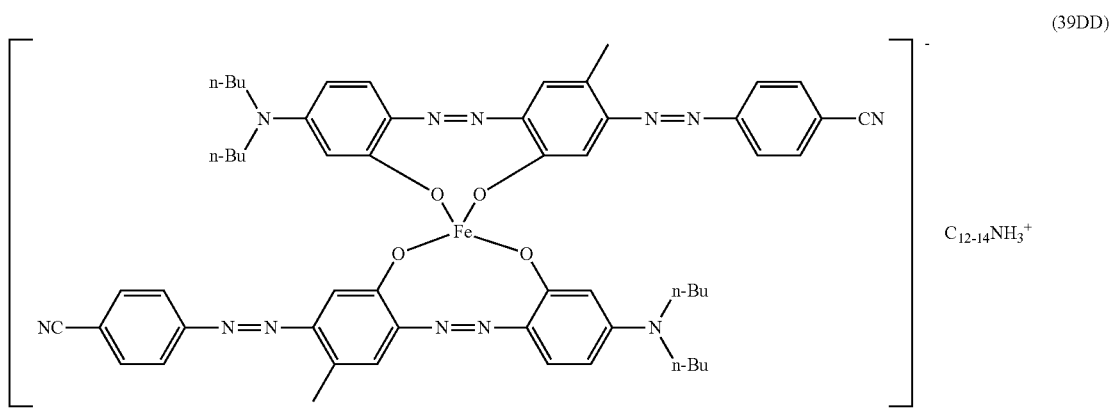

(39DD)

-continued $C_{12-14}NH_3^+$

The absorbance, the electrical conductivity, and the content of an alkaline metal ion of the azo iron complex dye B-1 were measured in the same manner as the azo iron complex dye A-1. A solution with the azo iron complex dye B-1 adjusted to a concentration of 5% exhibited a dark brown color. And the electrical conductivity K of the azo iron complex dye B-1 was 1450 μS/cm and the content of the alkaline metal ion was 1000 ppm or less.

Comparative Example 2: Preparation of Azo Iron Complex Dye B-2

To 100 g of N,N-dimethylformamide solution were added 21.9 g (moisture content 42%, 0.026 mol) of the disazo dye D-1 as a wet cake obtained in Preparation example 1 and 2.9 g of urea, and the mixture was stirred at 50° C. for 1 hour (disazo dye:monoazo dye=10:0 mol). To this mixture was added dropwise 6.33 g (0.007 mol) of 41% aqueous ferric sulfate solution, and, after completion of the dropwise addition, the mixture was heated to 120° C. and stirred for 3 hours. After completion of the reaction, the mixture was allowed to cool to room temperature, and then the pH was adjusted to 10.9 with 5.0 g of 20% aqueous sodium hydroxide solution. To this solution was added gradually 80.1 g of 5% aqueous solution of tert-alkyl ($C_{12}$-$C_{14}$) primary amine (available from Dow Chemical Co. Ltd.; trade name PRIMENE 81-R), and the mixture was stirred at 35° C. for 2 hours. Then the precipitate was filtered, washed with water, and dried. As a result, as represented by the following chemical formula (39DD), 9.41 g of the azo iron complex dye B-2 consisting of only the disazo-disazo iron complex was obtained.

The absorbance, the electrical conductivity, and the content of an alkaline metal ion of the azo iron complex dye B-2 were measured in the same manner as the azo iron complex dye A-1. When the azo iron complex dye B-2 was dissolved at a concentration of 5%, a sufficient black color was exhibited. But the azo iron complex dye B-2 had poor dissolution stability, and a precipitation was observed when left overnight (8 hours). And the electrical conductivity K of the azo iron complex dye B-2 immediately after dissolution was 165 μS/cm and the content of the alkaline metal ion was 1000 ppm or less.

Comparative Example 3: Preparation of Azo Iron Complex Dye B-3

Five parts by mass of the azo iron complex dye B-1 obtained in Comparative example 1 and 5 parts by mass of the azo iron complex dye B-2 obtained in Comparative example 2 were pulverized and mixed using an experimental mini-blender (available from AS ONE Corporation) to give 9.9 g of the azo iron complex dye B-3 which is a mixture of the azo iron complex dye B-1 and the azo iron complex dye B-2.

The absorbance, the electrical conductivity, and the content of an alkaline metal ion of the azo iron complex dye B-3 were measured in the same manner as the azo iron complex dye A-1. When the azo iron complex dye B-3 was dissolved at a concentration of 5%, a reddish black color was exhibited. And the electrical conductivity K of the azo iron complex dye B-3 was 979 μS/cm and the content of the alkaline metal ion was 1000 ppm or less.

(Comparison of Visible Absorption Spectra)

The visible absorption spectra of the azo iron complex dye A-1 obtained in Example 1 and the azo iron complex dyes B-1 to B-3 obtained in Comparative examples 1-3 are superimposed and shown in FIG. 8. The visible absorption spectrum of the azo iron complex dye B-1 is stronger than that of the azo iron complex dye A-1 in between 400 nm and 550 nm. This indicates that the azo iron complex dye B-1 exhibits a strong reddish tint.

The visible absorption spectrum of the azo iron complex dye B-2 has particularly strong absorption in the long wavelength region of 550 nm or more. This indicates that the azo iron complex dye B-2 exhibits a strong bluish tint The visible absorption spectrum of the azo iron complex dye B-3 showed almost the same visible absorption spectrum as the azo iron complex dye A-1. On the other hand, as described above, the azo iron complex dye A-1 exhibited a practically sufficient black color, while the azo iron complex dye B-3 exhibited a reddish black color. Comparing the spectra of both in detail, the visible absorption spectrum from 400 nm to 550 nm of the azo iron complex dye B-3 is higher than that of the azo iron complex dye A-1, while the absorbances from 600 nm to 650 nm are equivalent. This indicates that the DM-form contained only in the azo iron complex dye A-1 greatly contributes to the degree of blackness.

(Confirmation of Azo Iron Complex Dye Composition)

The azo iron complex dyes A-1 to A-7 to which the present invention is applied contain at least three kinds of the azo iron complexes of DM-, DD-, and MM-forms. Their relative abundance ratios (molar ratios) in the azo iron complexes can be determined from the peak area ratios in the chromatogram by measuring through high performance liquid chromatography (HPLC; available from Shimadzu Corporation, Prominence) at a specific wavelength. For the azo iron complex dyes A-1 to A-7 obtained in Examples 1-7 and the azo iron complex dyes B-1 to B-3 obtained in Comparative examples 1-3, 1 mg of each azo iron complex dye was dissolved in 10 ml of N,N-dimethylformamide solution and measured under the following measurement conditions. The results are shown in Table 4.

High Performance Liquid Chromatography:
 Column: L-COLUMN ODS2 4.6×250 mm, 5 μm
 Column temperature: 40° C.
Mobile Phase:

A liquid: tetrahydrofuran (available from FUJIFILM Wako Pure Chemical Corporation, HPLC grade)/acetonitrile (available from the same) =3/2

B liquid: ultrapure water/10 mM tetraethylammonium (available from Waters Corporation)=500/7.5

Gradient: A liquid/B liquid 50:50 to 70:30
Measurement wavelength: UV at 254 nm

TABLE 4

|  |  | Azo iron complex dye | D ligand | M ligand 1 | M ligand 2 | D dye/M dye 1/M dye 2 Charging mixing ratio (molar ratio) | DM form/MM form/DD form HPLC peak area ratio (molar ratio) |
|---|---|---|---|---|---|---|---|
| Example | 1 | A-1 | D-1 | M-1 | — | 2/8/0 | 40/59/1 |
|  | 2 | A-2 | D-1 | M-2 | — | 5/5/0 | 60/27/13 |
|  | 3 | A-3 | D-1 | M-3 | — | 2/8/0 | 22/76/2 |
|  | 4 | A-4 | D-2 | M-2 | — | 2/8/0 | 21/78/1 |
|  | 5 | A-5 | D-3 | M-2 | — | 4/6/0 | 44/48/8 |
|  | 6 | A-6 | D-1 | M-1 | M-2 | 2/4/4 | 30/69/1 |
|  | 7 | A-7 | D-3 | M-4 | — | 3/7/0 | 54/39/7 |
| Comparative example | 1 | B-1 | — | M-2 | — | 0/10/0 | 0/100/0 |

(Solubility Evaluation)

The azo iron complex dyes A-1 to A-7 obtained in Examples 1-7 and the azo iron complex dyes B-1 to B-3 obtained in Comparative examples 1-3 were put into methyl ethyl ketone and ethanol, respectively, at concentrations of 5%, 10%, 15% and 20% to prepare the azo iron complex dyes solutions, and ultrasonically dispersed for 10 minutes. Then the azo iron complex dyes solutions were filtered through a membrane filter (pore size 1 μm, PTFE) under reduced pressure, and the maximum concentrations of the azo iron complex dyes were defined as the concentrations at which it was confirmed that there were no insoluble substances on the membrane filter. Then the hue of the methyl ethyl ketone solution with the azo iron complex dyes concentrations of 5% was visually observed. The results are shown in Table 5.

TABLE 5

|  |  | Azo iron complex dye | Maximum concentration (%) | | Hue of 5% methyl ethyl ketone solution with azo iron complex dye |
|---|---|---|---|---|---|
|  |  |  | Methyl ethyl ketone | Ethanol |  |
| Example | 1 | A-1 | 15 | 10 | Black |
|  | 2 | A-2 | 10 | 5 | Black |
|  | 3 | A-3 | 10 | <5 | Black |
|  | 4 | A-4 | 10 | <5 | Black |
|  | 5 | A-5 | 20 | 15 | Purple |
|  | 6 | A-6 | 15 | 10 | Black |
|  | 7 | A-7 | 20 | 20 | Purple black |
| Comparative example | 1 | B-1 | 10 | 5 | Reddish brown (Brown) |
|  | 2 | B-2 | 5 | <5 | Black |
|  | 3 | B-3 | 10 | <5 | Reddish black |

By applying the present invention, in the azo iron complex dyes of Examples containing the disazo-monoazo iron complex as an essential, the hue of the 5% methyl ethyl ketone solution thereof exhibited a practical black color. In particular, the azo iron complex dyes A-1, A-2 and A-6, in which the disazo ligands have a cyano group and the monoazo ligands have a nitro group, respectively, exhibited high solubility in both methyl ethyl ketone and ethanol. The azo iron complex dye A-5, in which the disazo ligand has a sulfonamide group and the monoazo ligand has a nitro group, respectively, and the azo iron complex dye A-7, in which both the disazo ligand and the monoazo ligand have a sulfonamide group, had a slightly lower electrical conductivity and a slightly reddish hue, but exhibited high solubility in both methyl ethyl ketone and ethanol. The azo iron complex dye A-3, in which the monoazo ligand has a chlorine as a substituent, exhibited lower solubility in ethanol, but exhibited solubility in methyl ethyl ketone as high as 10% over the practical concentration of 6%.

In Comparative examples, which do not apply the present invention, the azo iron complex dye B-1 consisting of only the monoazo-monoazo iron complex exhibited good solubility, but exhibited a reddish brown hue instead of black. The azo iron complex dye B-2 consisting of only the disazo-disazo iron complex exhibited a black color within a practical range, but exhibited only low solubility in both methyl ethyl ketone and ethanol. In addition, due to poor dissolution stability in ethanol, when the ethanol solution of the azo iron complex dye B-2 was allowed to stand for 10 minutes, a precipitate was confirmed. The methyl ethyl ketone solution of the azo iron complex dye B-3 just by mixing the azo iron complex dye B-1 consisting of only the monoazo-monoazo iron complex and the azo iron complex dye B-2 consisting of only the disazo-disazo iron complex exhibited only a black color with a reddish tinge, and a precipitate was confirmed when its ethanol solution was allowed to stand for 10 minutes.

Ink Application Example 1

To 70 parts by mass of methyl ethyl ketone, 10 parts by mass of ethanol and 10 parts by mass of isopropyl alcohol were introduced 6 parts by mass of a cellulose resin, 1 part by mass of lithium nitrate and 3 parts by mass of the azo iron complex dye A-1, and the mixture was stirred and dissolved. Then the mixed solution was filtered through a filter with an opening of 1.0 μm to give the ink composition of Ink application example 1. This ink composition was filled in an ink cartridge and printed using an ink-jet printer to give a black print. The print was dark black with no fading. Judging from this result, the ink composition of Ink application example 1 was evaluated to have good print density and ink ejection stability.

Ink Application Example 2

Except that the azo iron complex dye A-2 was used instead of the azo iron complex dye A-1, the ink composition of Ink application example 2 was obtained in the same manner as Ink application example 1. The use of this ink composition gave a black print by operating in the same manner as Ink application example 1. The print was dark black with no fading. Judging from this result, the ink composition of Ink application example 2 was evaluated to have good print density and ink ejection stability.

Ink Application Example 3

Except that the azo iron complex dye A-5 was used instead of the azo iron complex dye A-1, the ink composition of Ink application example 3 was obtained in the same manner as Ink application example 1. The use of this ink composition gave a black print by operating in the same manner as Ink application example 1. The print was dark black with no fading. Judging from this result, the ink composition of Ink application example 3 was evaluated to have good print density and ink ejection stability.

Ink Application Example 4

Except that the azo iron complex dye A-6 was used instead of the azo iron complex dye A-1 and 0.5 parts by mass of triethanolamine was added as a pH adjuster, the ink composition of Ink application example 4 was obtained in the same manner as Ink application example 1. The use of this ink composition gave a black print by operating in the same manner as Ink application example 1. The print was dark black with no fading. Judging from this result, the ink composition of Ink application example 4 was evaluated to have good print density and ink ejection stability.

Ink Comparative Example 1

Except that the azo iron complex dye B-1 was used instead of the azo iron complex dye A-1, the ink composition of Ink comparative example 1 was obtained in the same manner as Ink application example 1. When this ink composition was used and printed on a printing medium by operating in the same manner as Ink application example 1, a light brown print with no opacity was obtained.

Ink Comparative Example 2

Except that the azo iron complex dye B-2 was used instead of the azo iron complex dye A-1, the ink composition of Ink comparative example 2 was obtained in the same manner as Ink application example 1. However, when this ink composition was allowed to stand for about 10 minutes, a precipitate was formed. This was removed by filtration. When this ink composition was used and printed on a printing medium by operating in the same manner as Ink application example 1, a thin black print was obtained.

Ink Comparative Example 3

Except that the azo iron complex dye B-3 was used instead of the azo iron complex dye A-1, the ink composition of Ink comparative example 3 was obtained in the same manner as ink application example 1. When this ink composition was used and printed on a printing medium by operating in the same manner as Ink application example 1, a light brown print with no opacity was obtained.

INDUSTRIAL APPLICABILITY

The azo iron complex dye of the present invention and the ink composition containing the same are used as an ink for an ink-jet printer, a writing instrument and a recorder. The method of the present invention for producing the azo iron complex dye is used for preparing the azo iron complex shown above.

What is claimed is:

1. An azo iron complex dye comprising:
a disazo-monoazo iron complex represented by the following chemical formula (1):

[Chemical Formula 1]

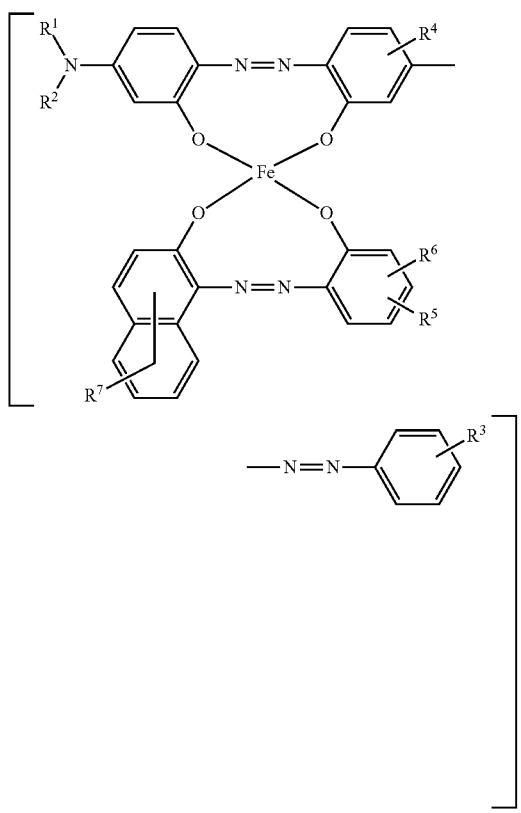

wherein, in the chemical formula (1), $R^1$ and $R^2$ are each independently a straight or branched alkyl group having 3-10 carbon atoms, $R^3$ is an electron-withdrawing group, $R^4$ is a straight or branched alkyl group having 1-5 carbon atoms or a straight or branched alkoxy group having 1-5 carbon atoms, $R^5$ is a nitro group, a sulfonamide group or a halogen atom, $R^6$ is a hydrogen atom, a straight or branched alkyl group having 1-8 carbon atoms, a nitro group or a halogen atom, $R^7$ is a hydrogen atom or a straight or branched alkyl group having 3-12 carbon atoms, and $A^+$ is a monovalent cation.

2. The azo iron complex dye according to claim 1, wherein $R^3$ is bonded at a para-position with respect to an azo group on the same aromatic ring, and is the electron-withdrawing group selected from the group consisting of a cyano group, a nitro group, an acetyl group, a sulfonamide group, and a halogen atom.

3. The azo iron complex dye according to claim 1, which contains a monoazo-monoazo iron complex represented by the following chemical formula (2):

[Chemical Formula 2]

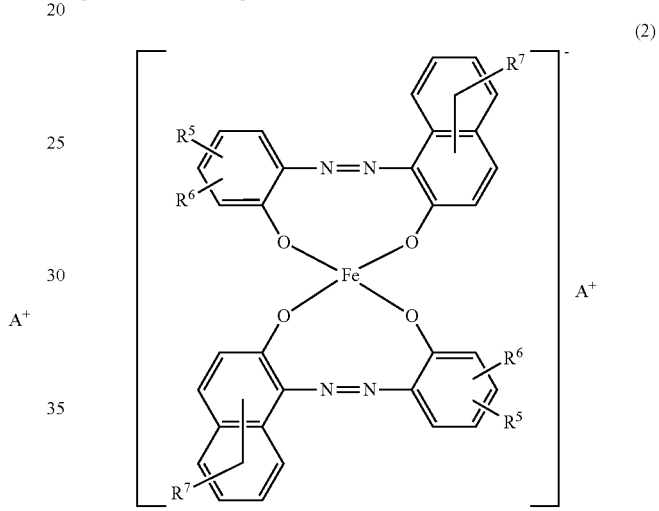

wherein, in the chemical formula (2), $R^5$-$R^7$ and $A^+$ are the same as ones of the chemical formula (1).

4. The azo iron complex dye according to claim 3, which contains the disazo-disazo iron complex represented by the following chemical formula (3):

[Chemical Formula 3]

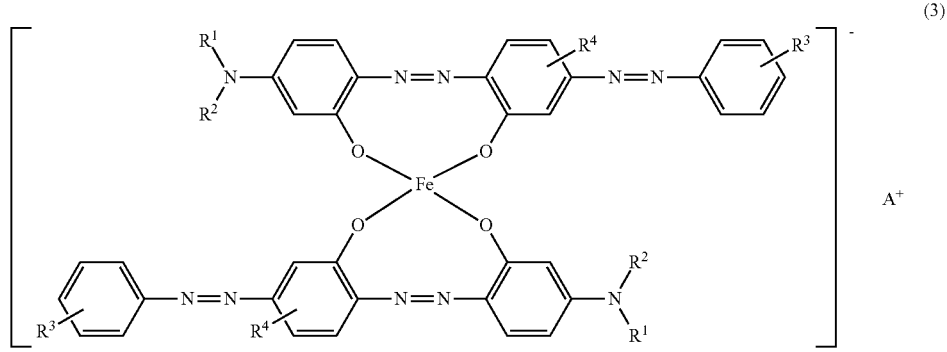

wherein, in the chemical formula (3), $R^1$-$R^4$ and $A^+$ are the same as ones of the chemical formula (1).

5. The azo iron complex dye according to claim 1, wherein the monovalent cation is any one of an alkali metal ion, an ammonium ion, a monovalent ammonium ion having an alkyl group represented by the following chemical formula (4):

[Chemical Formula 4]

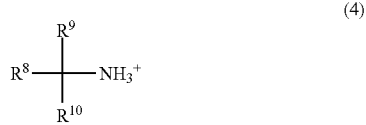
(4)

wherein, in the chemical formula (4), $R^8$ is a straight or branched alkyl group having 1-18 carbon atoms, and $R^9$ and $R^{10}$ are each independently a hydrogen atom or a straight or branched alkyl group having 1-8 carbon atoms.

6. The azo iron complex dye according to claim 4, wherein a peak area ratio of the chromatogram obtained by measuring the disazo-monoazo iron complex, the monoazo-monoazo iron complex, and the disazo-disazo iron complex at a wavelength of 254 nm through high performance liquid chromatography may be 20-70:5-80:0-50, respectively.

7. An ink composition comprising the azo iron complex dye according to claim 1, and an organic solvent.

8. The ink composition according to claim 7, which is used for an ink-jet printer.

9. A method for manufacturing an azo iron complex dye comprising:

a step for an iron-complexation for preparing an azo iron complex anion by heating a disazo dye represented by the following chemical formula (5):

[Chemical Formula 5]

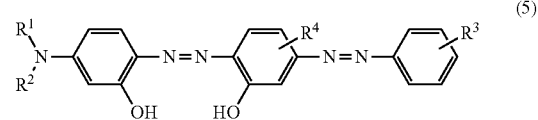
(5)

wherein, in the chemical formula (5), $R^1$ and $R^2$ are each independently a straight or branched alkyl group having 3-10 carbon atoms, $R^3$ is an electron-withdrawing group, $R^4$ is a straight or branched alkyl group having 1-5 carbon atoms or a straight or branched alkoxy group having 1-5 carbon atoms, a monoazo dye represented by the following chemical formula (6):

[Chemical Formula 6]

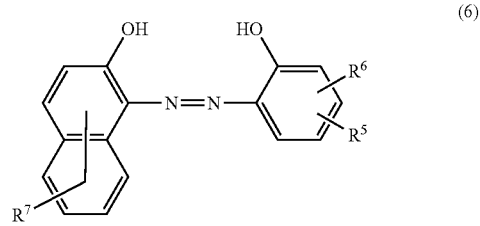
(6)

wherein, in the chemical formula (6), $R^5$ is a nitro group, a sulfonamide group or a halogen atom, $R^6$ is a hydrogen atom, a straight or branched alkyl group having 1-8 carbon atoms, a nitro group or a halogen atom, $R^7$ is a hydrogen atom or a straight or branched alkyl group having 3-12 carbon atoms, and an ironizing agent, in a solvent and, a step for ion-exchanging by reacting the azo iron complex anion, and an alkali metal solution and/or an ammoniation agent to introduce a cation which is combined with the azo iron complex anion, for obtaining a disazo-monoazo iron complex represented by the following chemical formula (1):

[Chemical Formula 7]

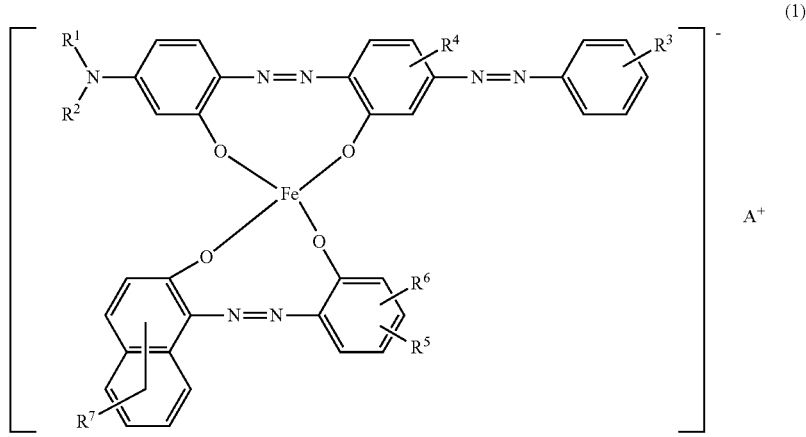
(1)

wherein, in the chemical formula (1), $R^1$-$R^4$ are the same as ones of the chemical formula (5), $R^5$-$R^7$ are the same as ones of the chemical formula (6), and $A^+$ is a monovalent cation.

10. The method for manufacturing the azo iron complex dye according to claim 9,
   wherein a molar ratio of the disazo dye and the monoazo dye is 2:8 to 8:2, in the step for the iron-complexation.

\* \* \* \* \*